(12) United States Patent
Brady et al.

(10) Patent No.: US 10,258,647 B2
(45) Date of Patent: Apr. 16, 2019

(54) IRON-POLYSACCHARIDE COMPLEXES AND METHODS FOR THE PREPARATION THEREOF

(71) Applicant: Particle Dynamics International, LLC, St. Louis, MO (US)

(72) Inventors: Paul Brady, St. Louis, MO (US); Keith Cromack, St. Louis, MO (US)

(73) Assignee: PARTICLE DYNAMICS INTERNATIONAL, LLC, St. Louis, MO (US)

( * ) Notice: Subject to any disclaimer, the term of this patent is extended or adjusted under 35 U.S.C. 154(b) by 103 days.

(21) Appl. No.: 15/251,062

(22) Filed: Aug. 30, 2016

(65) Prior Publication Data

US 2017/0056444 A1    Mar. 2, 2017

Related U.S. Application Data

(60) Provisional application No. 62/212,656, filed on Sep. 1, 2015.

(30) Foreign Application Priority Data

Jun. 2, 2016 (CA) .................................... 2932075

(51) Int. Cl.
  *A61K 33/26* (2006.01)
  *A61K 9/16* (2006.01)

(52) U.S. Cl.
  CPC ............ *A61K 33/26* (2013.01); *A61K 9/1652* (2013.01)

(58) Field of Classification Search
  CPC ..... A61K 33/26; A61K 9/1652; A61K 9/1611
  USPC ............................................ 514/23; 424/647
  See application file for complete search history.

(56) References Cited

U.S. PATENT DOCUMENTS

| | | |
|---|---|---|
| 3,766,165 A | 10/1973 | Rennhard et al. |
| 3,821,192 A | 6/1974 | Montgomery et al. |
| 4,226,983 A | 10/1980 | Lane |
| 4,576,818 A | 3/1986 | Shetty |
| 5,411,746 A | 5/1995 | Signorino et al. |
| 5,512,314 A | 4/1996 | Signorino et al. |
| 5,514,384 A | 5/1996 | Signorino |
| 5,595,592 A | 1/1997 | Signorino et al. |
| 5,601,863 A | 2/1997 | Borden et al. |
| 6,537,820 B2 | 3/2003 | Beck et al. |
| 6,559,302 B1 | 5/2003 | Shah et al. |
| 6,599,498 B1 | 7/2003 | Groman et al. |
| 7,754,702 B2 | 7/2010 | Helenek et al. |
| 8,193,291 B2 | 6/2012 | Zhang |
| 8,263,564 B2 | 9/2012 | Reim et al. |
| 8,273,393 B2 | 9/2012 | Rabovsky et al. |
| 8,409,463 B1 | 4/2013 | Perez et al. |
| 8,431,549 B2 | 4/2013 | Helenek et al. |
| 8,697,158 B2 | 4/2014 | Rabovsky et al. |
| 8,815,301 B2 | 8/2014 | Andreasen |
| 8,895,612 B2 | 11/2014 | Helenek et al. |
| 8,993,748 B2 | 3/2015 | Sacchi et al. |
| 2003/0124242 A1 | 7/2003 | Kiefer et al. |
| 2003/0191090 A1 | 10/2003 | Andreasen et al. |
| 2010/0247609 A1 | 9/2010 | Weibel et al. |
| 2011/0143007 A1 | 6/2011 | Stengel |
| 2014/0127351 A1 | 5/2014 | DiSilvestro |
| 2014/0296508 A1 | 10/2014 | Sacchi et al. |

FOREIGN PATENT DOCUMENTS

| | | |
|---|---|---|
| EP | 2626074 A1 | 8/2013 |
| GB | 928238 A | 6/1963 |
| JP | 2006101806 A | 4/2006 |
| WO | 0246241 A2 | 6/2002 |
| WO | 2010020321 A1 | 2/2010 |
| WO | 2010034319 | 4/2010 |
| WO | 2010108493 A1 | 9/2010 |
| WO | 2012104204 | 8/2012 |
| WO | 2014058516 | 4/2014 |

OTHER PUBLICATIONS

Coe et al. Comparison of Polysaccharide Iron Complexes Used as Iron Supplements. Journal of Inorganic Biochemistry, 57, 287-292 (1995) (Year: 1995).*
Tiihonen et al. Polydextrose functional fibre: Improving digestive health, satiety and beyond. NUTRA Foods 10(2-3):23-28, 2011. (Year: 2011).*
Andrade et al., "Coating Nanomagnetic Particles for Biomedical Applications," Biomedical Engineering, 2011, 2(5), pp. 157-176.
Anthony, Mark, "Understanding Polydextrose and How It Works," Food Processing, Oct. 1, 2012, accessed Nov. 14, 2014, <http://www.foodprocessing.com/articles/2012/understanding-polydextrose/>.
Beguin et al., "Iron sucrose—characteristics, efficacy and regulatory aspects of an established treatment of iron deficiency and iron-deficiency anemia in a broad range of therapeutic areas," Expert Opinion on Pharmacotherapy, Oct. 2014, 15(14), pp. 2087-2103.
Cortajarena et al., "Engineering Iron Oxide Nanoparticles for Clinical Settings," Nanobiomedicine, 2014, 1:2, 20 pages.

(Continued)

*Primary Examiner* — Yih-Horng Shiao
(74) *Attorney, Agent, or Firm* — Stinson Leonard Street LLP

(57) ABSTRACT

The present invention generally relates to iron-polysaccharide (polydextrose) complexes and methods for the preparation thereof. In particular, the present invention relates to iron-polydextrose complexes and methods for the preparation thereof. The inventive complexes are suitable for use in various compositions, including particulate compositions that may be incorporated in various forms of administration, including tablets, capsules, and intravenous formulations. The complexes and compositions of the present invention are suitable for use in the treatment of iron deficient anemia. Advantageously, in addition to providing iron supplementation the complexes and compositions of the present invention provide certain advantages based on the presence of polydextrose (e.g., its low glycemic index and high fiber content).

29 Claims, 18 Drawing Sheets

(56) References Cited

OTHER PUBLICATIONS

Danielson, Bo. G., "Structure, Chemistry, and Pharmacokinetics of Intravenous Iron Agents," Journal of the American Society of Nephrology, 2004, 15, pp. S93-S98.

"Dextrin," Wikipedia, 4 pages, accessed Nov. 14, 2014, <https://en.wikipedia.org/wiki/Dextrin>.

DeVries et al., "Polydextrose (trade name Litesse)," Technical Bulletin, Medallion Laboratories, 2 pages, Created: Jul. 19, 2007.

Dias et al., "A biotechnological perspective on the application of iron oxide magnetic colloids modified with polysaccharides," Biotechnology Advances, vol. 29, Issue 1, Jan.-Feb. 2011, pp. 142-155, (abstract).

Duguet, et al. "Synthesis and Characterisation of Iron Oxide Ferrite Nanoparticles and Ferrite-Based Aqueous Fluids in Magnetic Nanoparticles: From Fabrication to Clinical Applications" Thanh, Nguyen Ed.; CRC Press, 2012, pp. 47-72.

Elsayed et al., "Treatment of Anemia Progression via Magnetite and Folate Nanoparticles In Vivo," ISRN Nanotechnology, vol. 2014, Article ID 287575, 13 pages.

Fütterer et al., "Structural characterization of iron oxide/hydroxide nanoparticles in nine different parenteral drugs for the treatment of iron deficiency anaemia by electron diffraction (ED) and X-ray powder diffraction (XRPD)," Journal of Pharmaceutical and Biomedical Analysis 2013, 86, pp. 151-160.

"Glycemic index," Wikipedia, 5 pages, accessed Jun. 25, 2015, <https://en.wikipedia.org/wiki/Glycemic_index>.

Goldman et al., "Preliminary studies on a magneto-optical procedure for aligning RHIC magnets," Particle Accelerator Conference, 1993., 15th IEEE Particle Accelerator Conference, Washington, DC, USA, May 17-20, 1993, pp. 2916-2918.

Graczykowski et al., "Iron-dextran complex: geometrical structure and magneto-optical features," Journal of Colloid and Interface Science, 2011, 363, pp. 551-556.

Gupta et al., "Synthesis and surface engineering of iron oxide nanoparticles for biomedical applications," Biomaterials, 2005, 26, pp. 3995-4021.

Hasany et al., "Systematic Review of the Preparation Techniques of Iron Oxide Magnetic Nanoparticles," Nanoscience and Nanotechnology, 2012, 2(6), pp. 148-158.

Jahn et al., "A comparative study of the physicochemical properties of iron isomaltoside 1000 (Monofer), a new intravenous iron preparation and its clinical implications," European Journal of Pharmaceutics and Biopharmaceutics, 2011, 78, pp. 480-491.

Kudasheva et al., "Structure of carbohydrate-bound polynuclear iron oxyhydroxide nanoparticles in parenteral formulations," Journal of Inorganic Biochemistry, 2004, 98, pp. 1757-1769.

Laurent et al., "Magnetic Iron Oxide Nanoparticles: Synthesis, Stabilization, Vectorization, Physicochemical Characterizations, and Biological Applications," Chemical Reviews 2008, 108, pp. 2064-2110.

"Litesse Polydextrose," Bibliography, DuPont Nutrition & Health, Version Aug. 2013, 12 pages.

Lu et al., "Magnetic Nanoparticles: Synthesis, Protection, Functionalization, and Application," Angewandte Chemie-International Edition, 2007, 46, pp. 1222-1244.

Mahmoudi et al., "Recent Advances in Surface Engineering of Superparamagnetic Iron Oxide Nanoparticles for Biomedical Applications," Journal of the Iranian Chemical Society, Jul. 2010, vol. 7, Suppl., pp. S1-S27.

Martin et al., "Determination of the Oxide Layer Thickness in Core-Shell Zerovalent Iron Nanoparticles," Langmuir 2008, 24, pp. 4329-4334.

Neiser et al., "Physico-chemical properties of the new generation IV iron preparations ferumoxytol, iron isomaltoside 1000 and ferric carboxymaltose," Biometals, 2015, 28(4), pp. 615-635.

Pai et al., "Ferumoxytol: a silver lining in the treatment of anemia of chronic kidney disease or another dark cloud?," Journal of Blood Medicine, 2012, 3, pp. 77-85.

Santos, Elisvânia Freitas dos et al., "Ingestion of polydextrose increase the iron absorption in rats submitted to partial gastrectomy," Acta Cirargica Brasileira, 2010, vol. 25(6), pp. 518-524.

Sipos et al., "Rod-Like Iron(III) Oxyhydroxide Particles in Iron (III)-Polysaccharide Solutions," Journal of Inorganic Biochemistry, May 1, 1995, vol. 58, Issue 2, pp. 129-138.

Somsook et al., "Interactions between iron(III) and sucrose, dextran, or starch in complexes," Carbohydrate Polymers, vol. 61, Issue 3, Aug. 29, 2005, pp. 281-287.

Sugahara et al., "A colloidal solution of Fe3O4 crystallites to optically locate the magnetic center of multipole magnets," KEK report, 89-9, Sep. 1989, 9 pages.

Tiihonen et al., "Polydextrose functional fibre: Improving digestive health, satiety and beyond," Nutrafoods, 2011, 10 (2-3), pp. 23-28.

"Trimcal Polydextrose Powder," Product Information, C&H Ingredients, Ingredients for Food Health Sport, accessed Nov. 14, 2014, <http://www.candhingredients.co.uk/productinformation.php?product=1>.

Uthaman et al., "Polysaccharide-Coated Magnetic Nanoparticles for Imaging and Gene Therapy", BioMed Research International, 2015, Article ID 959175, 14 pages.

Wahajuddin et al., "Superparamagnetic iron oxide nanoparticles: magnetic nanoplafforms as drug carriers," International Journal of Nanomedicine, 2012, 7, pp. 3445-3471.

Zhang et al., "Optimization of Process Conditions for Preparing an Iron-polysaccharide Complex by Response Surface Methodology," Chem. Biochem. Eng., 2011, vol. 25, Issue 1, pp. 75-81.

International Search Report and Written Opinion, PCT/IB2016/055178, dated Nov. 23, 2016, 10 pages.

International Preliminary Report on Patentability, PCT/IB2016/055178, dated Nov. 28, 2017, 14 pages.

Bereman et al., "The Structure, Size and Solution Chemistry of a Polysaccharide Iron Complex (Niferex)," Inorganica Chimica Acta, vol. 155, Issue 2, Jan. 16, 1989, pp. 183-189.

\* cited by examiner

FIG. 4

| Mesh No | Aperture μm | Volume in % | Vol Below % |
|---|---|---|---|
| 10 | 2000 | | 100.00 |
| 12 | 1700 | 0.00 | 100.00 |
| 14 | 1400 | 0.00 | 100.00 |
| 16 | 1180 | 0.00 | 100.00 |
| 18 | 1000 | 0.00 | 100.00 |
| 20 | 850 | 0.00 | 100.00 |
| 25 | 710 | 0.00 | 100.00 |
| 30 | 600 | 0.00 | 100.00 |
| 35 | 500 | | |

| Mesh No | Aperture μm | Volume in % | Vol Below % |
|---|---|---|---|
| 35 | 500 | | 100.00 |
| 40 | 425 | 0.00 | 100.00 |
| 45 | 355 | 0.00 | 100.00 |
| 50 | 300 | 0.00 | 100.00 |
| 60 | 250 | 0.00 | 100.00 |
| 70 | 212 | 0.00 | 100.00 |
| 80 | 180 | 0.00 | 100.00 |
| 100 | 150 | 0.00 | 100.00 |
| 120 | 125 | | |

| Mesh No | Aperture μm | Volume in % | Vol Below % |
|---|---|---|---|
| 120 | 125 | | 100.00 |
| 140 | 106 | 0.00 | 100.00 |
| 170 | 90 | 0.00 | 100.00 |
| 200 | 75 | 0.00 | 100.00 |
| 230 | 63 | 0.00 | 100.00 |
| 270 | 53 | 0.00 | 100.00 |
| 325 | 45 | 0.00 | 100.00 |
| 400 | 38 | 0.29 | 99.71 |

FIG. 6

| Mesh No | Aperture μm | Volume in % | Vol Below % |
|---|---|---|---|
| 10 | 2000 | 0.00 | 100.00 |
| 12 | 1700 | 0.00 | 100.00 |
| 14 | 1400 | 0.00 | 100.00 |
| 16 | 1180 | 0.00 | 100.00 |
| 18 | 1000 | 0.00 | 100.00 |
| 20 | 850 | 0.00 | 100.00 |
| 25 | 710 | 0.00 | 100.00 |
| 30 | 600 | 0.00 | 100.00 |
| 35 | 500 | 0.00 | 100.00 |

| Mesh No | Aperture μm | Volume in % | Vol Below % |
|---|---|---|---|
| 35 | 500 | 0.00 | 100.00 |
| 40 | 425 | 0.00 | 100.00 |
| 45 | 355 | 0.00 | 100.00 |
| 50 | 300 | 0.00 | 100.00 |
| 60 | 250 | 0.00 | 100.00 |
| 70 | 212 | 0.00 | 100.00 |
| 80 | 180 | 0.00 | 100.00 |
| 100 | 150 | 0.00 | 100.00 |
| 120 | 125 | 0.00 | 100.00 |

| Mesh No | Aperture μm | Volume in % | Vol Below % |
|---|---|---|---|
| 120 | 125 | 0.00 | 100.00 |
| 140 | 106 | 0.00 | 100.00 |
| 170 | 90 | 0.00 | 100.00 |
| 200 | 75 | 0.00 | 100.00 |
| 230 | 63 | 0.00 | 100.00 |
| 270 | 53 | 0.00 | 100.00 |
| 325 | 45 | 0.08 | 99.92 |
| 400 | 38 | 0.65 | 99.27 |

FIG. 8

| Mesh No | Aperture μm | Volume in % | Vol Below % |
|---|---|---|---|
| 10 | 2000 |  | 100.00 |
| 12 | 1700 | 0.00 | 100.00 |
| 14 | 1400 | 0.00 | 100.00 |
| 16 | 1180 | 0.00 | 100.00 |
| 18 | 1000 | 0.00 | 100.00 |
| 20 | 850 | 0.00 | 100.00 |
| 25 | 710 | 0.00 | 100.00 |
| 30 | 600 | 0.00 | 100.00 |
| 35 | 500 | 0.00 | 100.00 |

| Mesh No | Aperture μm | Volume in % | Vol Below % |
|---|---|---|---|
| 35 | 500 |  | 100.00 |
| 40 | 425 | 0.00 | 100.00 |
| 45 | 355 | 0.00 | 100.00 |
| 50 | 300 | 0.00 | 100.00 |
| 60 | 250 | 0.00 | 100.00 |
| 70 | 212 | 0.00 | 100.00 |
| 80 | 180 | 0.00 | 100.00 |
| 100 | 150 | 0.00 | 100.00 |
| 120 | 125 |  | 100.00 |

| Mesh No | Aperture μm | Volume in % | Vol Below % |
|---|---|---|---|
| 120 | 125 |  | 100.00 |
| 140 | 106 | 0.00 | 100.00 |
| 170 | 90 | 0.00 | 100.00 |
| 200 | 75 | 0.00 | 100.00 |
| 230 | 63 | 0.00 | 100.00 |
| 270 | 53 | 0.00 | 100.00 |
| 325 | 45 | 0.31 | 99.69 |
| 400 | 38 | 0.99 | 98.70 |

IRON-POLYSACCHARIDE COMPLEXES AND METHODS FOR THE PREPARATION THEREOF

REFERENCE TO RELATED APPLICATIONS

This application claims priority to U.S. Provisional Application Ser. No. 62/212,656, filed Sep. 1, 2015 and Canadian Application Serial No. 2,932,075, filed Jun. 2, 2016, the entire disclosures of which are hereby incorporated by reference.

FIELD OF THE INVENTION

The present invention generally relates to iron-polysaccharide (polydextrose) complexes and methods for the preparation thereof. In particular, the present invention relates to iron-polydextrose complexes and methods for the preparation thereof. The inventive complexes are suitable for use in various compositions, including particulate compositions that may be incorporated in various forms of administration, including tablets, capsules, and intravenous formulations. The complexes and compositions of the present invention are suitable for use in the treatment of iron deficient anemia. Advantageously, in addition to providing iron supplementation the complexes and compositions of the present invention provide certain advantages based on the presence of polydextrose (e.g., its low glycemic index and high fiber content).

BACKGROUND OF THE INVENTION

Iron-polysaccharide complexes are known in the art and are often of interest due to their value for the treatment of iron deficient anemia. Various iron-polysaccharide complexes are currently used clinically to improve iron levels in patients with low iron levels and also may be used to prevent iron deficient anemia. Effective polysaccharide iron complex (PIC) products are known in the art. These include PIC prepared from corn syrup and sorbitol. Such PIC products are known to be suitable for use in preparing effective iron supplements, but they may suffer from one or more disadvantages. For example, the reaction between corn syrup and sorbitol is believed to occur at iron sites and may result in formation of uncontrolled final structures. The final PIC product may also include certain impurities remaining from the process (e.g., unreacted maltose).

Although effective PIC products are known in the art, there exists a need in the art for alternative iron-polysaccharide complexes that may overcome one or more disadvantages of conventional PIC products and/or provide certain advantages based on the nature of the particular complex.

SUMMARY OF THE INVENTION

Briefly, therefore, the present invention is directed to iron-polysaccharide complexes (e.g., iron-polydextrose complexes) and methods for the preparation thereof. The iron-polysaccharide complexes are suitable for use in preparation of particulate compositions that may be incorporated into various forms of administration (e.g., tablets, capsules, and intravenous formulations). The present invention is further directed to methods for treatment of iron deficient anemia by administration of a complex or composition of the present invention. The present invention is still further directed to methods for treatment of iron deficient anemia in combination with treatments for type-2 diabetes and/or methods for treatment of iron deficient anemia brought on by treatment for type-2 diabetes. Further treatment methods of the present invention include treatment of constipation, both separately and in combination with iron supplementation, including constipation that may be brought on by a variety of factors. Treatment methods of the present invention further include those for fiber supplementation.

In certain embodiments, the present invention is directed to a particulate composition comprising an iron-polydextrose complex, wherein the iron-polydextrose complex is characterized by either or both of the following structures:

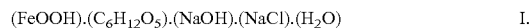

$$(FeOOH).(C_6H_{12}O_5).(NaOH).(NaCl).(H_2O) \quad \text{I.}$$

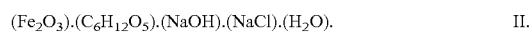

$$(Fe_2O_3).(C_6H_{12}O_5).(NaOH).(NaCl).(H_2O). \quad \text{II.}$$

In further embodiments, the present invention is directed to a particulate composition comprising an iron-polydextrose complex, wherein the iron-polydextrose complex is characterized by either or both of the following structures:

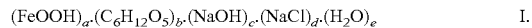

$$(FeOOH)_a.(C_6H_{12}O_5)_b.(NaOH)_c.(NaCl)_d.(H_2O)_e \quad \text{I.}$$

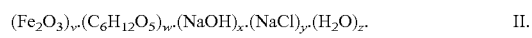

$$(Fe_2O_3)_v.(C_6H_{12}O_5)_w.(NaOH)_x.(NaCl)_y.(H_2O)_z. \quad \text{II.}$$

In other embodiments, the present invention is directed to a particulate composition comprising an iron-polydextrose complex, wherein the iron (Fe) content of the composition is at least about 30 wt %; and the ratio of C:Fe, as determined by elemental analysis, is at least 0.2:1.

In further embodiments, the present invention is directed to particulate compositions comprising an iron-polydextrose complex, wherein the polydextrose is characterized as comprising dextrose units bonded by 1,2-glycosidic linkages, 1,4-glycosidic linkages, and 1,6-glycosidic linkages; and the complex is substantially free of furanose.

The present invention is also directed to methods for the preparation of an iron-polysaccharide complex. In certain embodiments, the method comprises introducing into an aqueous medium a source of iron (III) ions and a polysaccharide comprising polydextrose, thereby forming an aqueous reaction medium comprising Fe(III) ions and polydextrose; introducing into the aqueous reaction medium a first source of hydroxide ions and mixing the contents of the reaction medium, thereby forming Fe(III)oxyhydroxide; and introducing into the aqueous reaction medium a second source of hydroxide ions and mixing the contents of the reaction medium, thereby forming the iron-polysaccharide complex, wherein the temperature of the reaction medium does not increase more than about 40° C. from addition of the first source of hydroxide ions to completion of the mixing following introduction of the second source of hydroxide ions.

In other embodiments, the method comprises introducing into an aqueous medium a source of iron (III) ions and a polysaccharide comprising polydextrose, thereby forming an aqueous reaction medium comprising Fe(III) ions and polydextrose; introducing into the aqueous reaction medium a first source of hydroxide ions and mixing the contents of the reaction medium; and introducing into the aqueous reaction medium a second source of hydroxide ions and mixing the contents of the reaction medium, wherein the temperature of the reaction medium during the second addition of hydroxide ions and mixing is no greater than about 90° C.

Other objects and features will be in part apparent and in part pointed out hereinafter.

BRIEF DESCRIPTION OF DRAWINGS

FIGS. 3 and 4 provide the results of particle size analysis as described in Example 3.

FIGS. 5 and 6 provide the results of particle size analysis as described in Example 4.

FIGS. 7-9 provide the results of particle size analysis as described in Example 5.

DETAILED DESCRIPTION OF THE PREFERRED EMBODIMENTS

Figure 1:
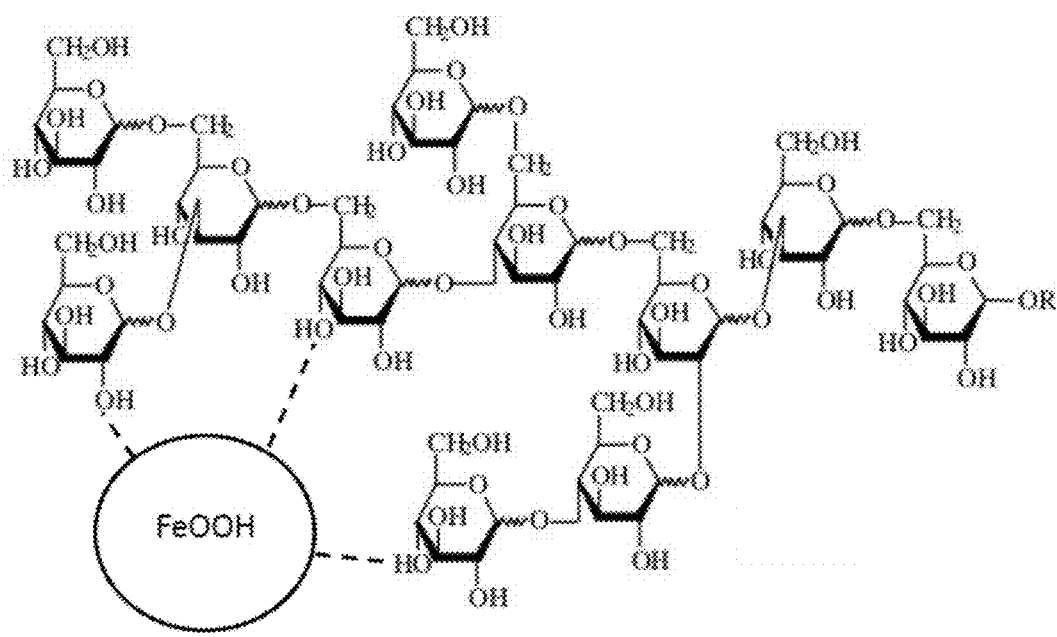
FIG. 1 graphically displays an iron-polydextrose complex (PDIC) of the present invention.

Described herein are advantageous iron-polysaccharide complexes and methods for the preparation thereof. Generally, the iron-polysaccharide complexes detailed herein include iron as iron (III) ions and include the polysaccharide polydextrose.

The iron-polydextrose complexes of the present invention are suitable for use in the treatment of iron deficient anemia. The iron-polydextrose complexes of the present invention introduce various advantages over conventional iron supplements. Certain of these benefits relate to the use and presence of polydextrose. For example, polydextrose is known to have a relatively low glycemic index (GI), in particular a glycemic index of no more than 10% of natural sugar and typically less than 10. This low glycemic index of polydextrose is advantageous in and of itself in that consumers often prefer such compositions in order to avoid consuming excess or unnecessary sugars because of their high calorie content.

Polydextrose's low GI also is currently believed to render the complexes and compositions of the present invention suitable for particular applications. A common side-effect of treatment of type-2 diabetes is iron deficient anemia. The complexes of the present invention may be used to treat iron deficient anemia in such patients. Low glycemic index foods or products cause a gradual rise in glucose levels and limit spikes in insulin levels, which is advantageous for diabetic patients. The use of polydextrose and its low-glycemic index profile may therefore be used for treatment of iron deficient anemia for type-2 diabetes treatment patients without adverse effects on glucose levels for these patients.

Subjects that have undergone bariatric surgery typically have difficulty absorbing iron salts, if any ability at all. It is currently believed that the iron-polydextrose formulations of the present invention are suitable for iron supplementation for such patients because of the ease in which the formulations are digested. An additional benefit for this patient population is the low calorie/low glycemic index nature of the iron-polydextrose formulations of the present invention.

Polydextrose is a soluble, non-viscous synthetic polymer that is only partially fermented by gut microbiota. In contrast, other soluble polymers, such as inulin, promote the growth of bifidogenic bacteria and are efficiently fermented by gut microbes. The only partial fermentation of polydextrose renders it available in a subject's gut to provide beneficial effects.

Also, polydextrose is a soluble fiber with the ability to bind water and therefore may be employed as a partial or total sugar replacement. As a synthetic compound polydextrose is not subject to natural compositional variations that may be attendant natural products such as corn sugar. In addition, because polydextrose is only partially metabolized in the human digestive system it's energy value is significantly lower than that of sugar (i.e., approximately 1 kcal/g versus 4 kcal/g).

The presence of fiber in polydextrose provides certain advantages noted above as compared to other polysaccharides that do not contain fiber. A common side-effect of iron deficient anemia treatment with conventional iron supplements is constipation. The effectiveness of polydextrose as a fiber supplement is currently believed to render it effective for treatment of this condition. The polydextrose is only partly metabolized and in this manner promotes bowel movements and alleviation of constipation.

Polydextrose in the compositions of the present invention is also believed to provide advantageous performance as a fiber supplement as compared to other fiber supplements, at least in part based on the high fiber content of polydextrose. This improved fiber supplement performance may be combined with iron supplementation to provide both advantageous fiber supplementation and iron supplementation (e.g., treatment of iron deficient anemia).

Figure 2:
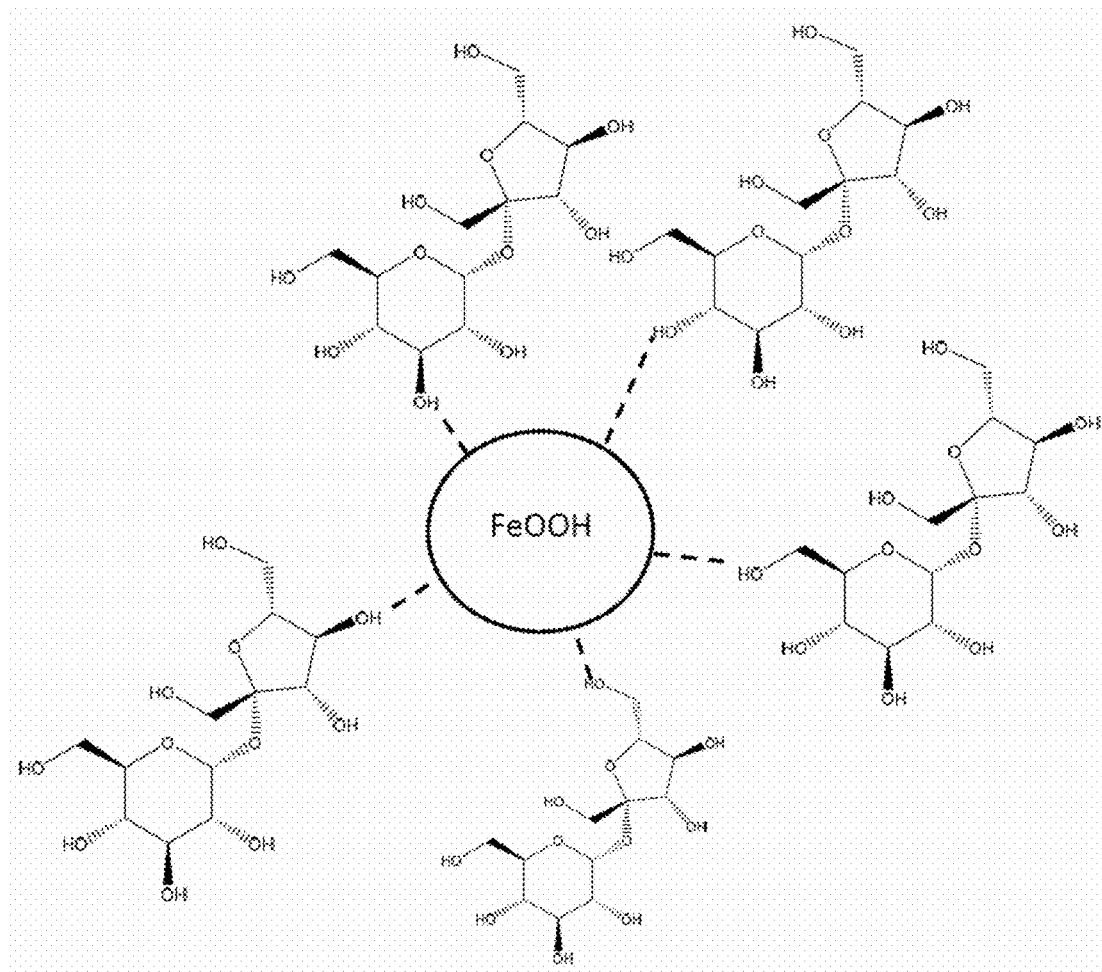
FIG. 2 graphically displays a polysaccharide iron complex (PIC).

The complexes of the present invention are also believed to involve the presence of a greater proportion of carbon within the iron-polydextrose complex as compared to other iron-polysaccharide complexes (e.g., PIC compositions described herein). This feature may be expressed either as the ratio of carbon to iron (C:Fe) or the proportion of C itself, each as determined by elemental analysis. This greater proportion of carbon is generally believed to indicate a greater proportion of sugars (e.g., the dextrose components of the polydextrose) present within the complexes of the present invention. Generally, this feature is provided by the polymeric polydextrose being bound to an iron-containing core in the complexes of the present invention as compared to individual sugar molecules being bound to iron molecules or iron-containing cores in conventional iron-polysaccharide complexes (e.g., iron-sucrose complexes). FIGS. 1 and 2 graphically display this concept and compare a complex of the present invention (often referred to herein as PDIC, or a PDIC complex) (FIG. 1) and a conventional iron-polysaccharide complex (often referred to herein as PIC, or a PIC complex) (FIG. 2). As further detailed herein, the complexes of the present invention may exhibit a greater proportion of "surface carbon" evidencing the presence of polydextrose surrounding the iron-containing cores to a greater extent than in conventional iron-polysaccharide complexes such as, for example, PIC complexes. Concomitantly, the complexes of the present invention may exhibit reduced exposed "surface iron" as compared to other iron-polysaccharide complexes.

Iron-Polysaccharide (Iron (Iron (III))-Polydextrose) Complexes

Generally, the iron polydextrose complexes of the present invention include iron as iron (III) ions and polydextrose, with iron ions and polydextrose bonded together, directly or indirectly. The polydextrose generally includes straight and branched chains. It is currently believed that iron (III) ions are present in the inventive complex in multiple forms and one or more of these forms are bonded, directly or indirectly with the polydextrose. For example, during preparation of the complex Fe(III) ions form Fe(III)-oxyhydroxide, which is then bonded to the polydextrose. In particular, it is currently believed that the Fe(III)-oxyhydroxide is bonded at its hydroxyl, oxy, and metal sites to hydroxyl sites of the polydextrose.

The bonds between the Fe(III) oxyhydroxide and the polydextrose may be hydrogen and/or covalent bonds. Additionally or alternatively, Fe(III) oxyhydroxide and the polydextrose may be joined in the form of a chelate with polydextrose ligands coordinated to the Fe(III) oxyhydroxide.

Fe(III) ions that have not formed Fe(III) oxyhydroxide may also be present in the Fe(III)-polydextrose complex. The Fe(III) ions may be bonded to the polydextrose at hydroxyl and carboxylic acid sites on the polydextrose by hydrogen and/or covalent bonds.

The inventive complexes detailed herein are referred to as "iron-polydextrose complexes." This designation at least indicates the use of polydextrose in the preparation of the inventive compositions and polydextrose is currently believed to be present in the final complexes and compositions of the present invention. It is to be understood, however, that the inventive complexes are also properly defined as "iron-polysaccharide" complexes as defined by certain features associated with polydextrose (e.g., dextrose units bonded by 1,2-glycosidic linkages, 1,4-glycosidic linkages, and 1,6-glycosidic linkages and others included in the appended claims) and various features determined by characterization of the resulting complexes (e.g., elemental analysis). Compositions defined in this manner are likewise part of the invention and the discussion of any features or uses of "iron(III)-polydextrose" complexes herein likewise apply to such "iron-polysaccharide" complexes.

Generally, the polysaccharide (polydextrose) of the complexes of the present invention includes alpha and beta glycosidic linkages. In particular, in certain embodiments, the polysaccharide is defined as comprising dextrose units bonded by 1,2-glycosidic linkages, 1,4-glycosidic linkages, and 1,6-glycosidic linkages. 1,6-Glycosidic linkages are believed to constitute a majority of the polysaccharide linkages. In any event, all three types of linkages are present in polydextrose. Each of these three types of linkages however is not present in other polysaccharides such as, for example, dextrin and dextran. Reaction of corn syrup with sorbitol does not result in a polysaccharide with each type of linkage.

Polydextrose itself generally does not contain furanose (5-membered sugars). However, commercial sources of polydextrose may contain minor amounts of furanose, but typically no more than about 0.1 weight % furanose (5-(hydroxymethyl)furfural), if any at all. Therefore, iron-polydextrose complexes of the present invention prepared therefrom are generally at least substantially free of such sugars.

In addition, as compared to other polysaccharides, polydextrose includes both straight and branched chains. The presence of these branched chains is currently believed to provide complexity which prevents mammalian digestive enzymes from readily hydrolyzing the molecule. The branched chains of the polydextrose may hinder crystallization and lower surface packing of the polydextrose.

In current PIC products utilizing a polysaccharide prepared from corn syrup and sorbitol, multiple —OH and —O sites on the polysaccharide are believed to interact with the Fe(III) ions or Fe(III)oxyhydroxide. Similar interaction of —OH and —O sites on the polydextrose with Fe(III) ions is believed to occur in the inventive complexes. However, the higher purity and more ordered arrangement of the polydextrose are believed to result in a more controlled end product that may provide one or more advantages. For example, these features may result in particulate products exhibiting more controlled particle size distribution. These features may also provide greater solubility and absorption as compared to conventional PIC products.

Additionally or alternatively, in certain embodiments, the polysaccharide may be characterized as non-reactive to anti-dextran antibodies. This feature is particularly advantageous in connection with intravenous formulations including complexes and/or compositions of the present invention. In particular, resistance to anti-dextran antibodies present in the blood where direct interaction occurs with the complex in an intravenous formulation may be particularly advantageous.

Polydextrose utilized in accordance with the present invention may be either food-grade or pharmaceutical grade. Each type is suitable. Food grade polydextrose provides cost advantages while pharmaceutical grade polydextrose may provide advantages in terms of its low impurity profile.

Both food grade and pharmaceutical grade polydextrose typically contain impurities such as glucose, sorbitol, citric acid, phosphoric acid and/or levoglucosan. Levoglucosan is described as 1,6-anhydro-beta-glucopyranose. Typically, the polydextrose contains no more than about 5 weight % free glucose, no more than about 2 weight % free sorbitol, no more than about 0.1 weight % citric acid and no more than about 5 weight % free levoglucosan.

As noted, the polydextrose has a low glycemic index, which is advantageous for many reasons including the fact that it will cause a gradual rise in glucose levels and limit spikes in insulin levels, which is advantageous for diabetic patients. The low glycemic index is based on the fact that the polydextrose is only partially metabolized in the body and does not break down into individual glucose molecules. Typically, the pharmaceutical grade polydextrose has a glycemic index of less than about 10, less than about 8, or less than about 6.

The polydextrose polymer comprises straight and branched chains with a random assortment of alpha and beta glycosidic linkages, of which the 1,6-glycosidic linkage constitute the majority. Additionally, the polydextrose is non-reactive to anti-dextran antibodies. Typically, the average degree of polymerization of the polydextrose utilized in accordance with the present invention is from about 10 to about 15. The molecular weight of suitable polydextrose molecules typically is from about 162 to about 20,000 Da and about 90% (by weight) of the polydextrose molecules have a molecular weight from about 500 to about 5,000 Da. The average molecular weight of the incorporated polydextrose typically is from about 1,800 to about 2,200 Da. In certain embodiments, the polydextrose may be comprised of about 90 parts dextrose, about 10 parts sorbitol, and about 1 part citric acid or about 0.1 part phosphoric acid.

It is currently believed that the complexes of the present invention include a core including iron oxyhydroxide (FeOOH) molecules. Generally, iron oxyhydroxide molecules are bonded to the polydextrose in a manner such that a core of these molecules is surrounded by the polydextrose in a shell-like manner. The iron oxyhydroxide within the complex may contain Fe(III) coordinated by two oxygen atoms at an average bond distance of about 1.9 Å. In certain embodiments, Fe(III) may be coordinated by two oxygen atoms. The core may also include iron oxide molecules in the form of both $Fe_2O_3$ or FeO (ferrous oxide), but $Fe_2O_3$ (ferric oxide) is typically the predominant and more typically the major iron oxide component. The core also may include "free" iron atoms not present as either iron oxyhydroxide or iron oxide.

As noted above, polydextrose is bonded, directly or indirectly, to Fe(III) atoms and/or Fe(III)-oxyhydroxide in a manner that the polydextrose surrounds each of these portions of the complex. That is, the outer or surrounding layer(s) are made up of polydextrose that surrounds a core defined by Fe(III) and/or Fe(III)-oxyhydroxide. In any case, the arrangement of the Fe(III)-oxyhydroxide-containing core is currently believed to be spheroid, ellipsoid, spherical, or rod-like in shape.

Generally, the Fe(III)-oxyhydroxide polydextrose complex has a molecular weight of from about 10 KDa to about 200,000 KDa. Typically, the molecular weight of the Fe(III)-oxyhydroxide polydextrose complex is from about 10 KDa to about 100,000 KDa, from about 100 to about 50,000 kDa, from about 500 about 25,000 KDa, or from about 5000 to about 20,000 KDa (e.g., about 10,000 KDa).

The iron content of a complex of the present invention is generally at least about 25 weight %, at least about 30 weight %, at least about 35 weight %, or at least about 40 weight %. Typically, the iron content of the complex of the present invention is from about 20 to about 50 weight %, from about 30 to about 50 weight %, or from about 35 to about 45 weight %.

The Fe(III)-oxyhydroxide content of a complex of the present invention is typically from about 50 to about 95 weight %, from about 50 to about 70 weight %, or from about 55 to about 65 weight %.

Generally, the weight ratio of iron (III) to polydextrose within the complex is from about 0.1:1 to about 10:1, from about 0.3:1 to about 3:1, or from about 0.5:1 to about 2:1.

The polysaccharide (polydextrose) content of a complex of the present invention is generally at least about 5 weight %, at least about 10 weight %, at least about 20 weight %, or at least about 30 weight %. Typically, the polysaccharide content of a complex of the present invention is from about 5 to about 40 weight %, from about 10 to about 40 weight %, from about 20 to about 40 weight %, or from about 20 to about 30 weight %.

As detailed elsewhere herein, sorbitol may be introduced during preparation of the complex to promote cross-linking between the Fe(III)oxyhydroxide and the polydextrose. If utilized, sorbitol is typically present in the complex in a weight ratio of sorbitol to polydextrose of from about 0.1:1 to about 0.5:1, or from about 0.1:1 to about 0.4:1. Any sorbitol is typically introduced along with the polydextrose, or nearly immediately thereafter.

The fiber content of polydextrose is typically at least about 80% or at least about 90%. This fiber content, as compared to other polysaccharide polymers, is advantageous for many reasons, e.g., it alters how nutrients and chemicals are absorbed in the digestive tract, attenuates the absorption of sugar, lowers cholesterol levels in the blood, and can be fermented in the colon to produce short-chain fatty acids as byproducts. Additionally, fermentation of polydextrose can lead to an increase in growth of favorable microflora and suppressed production of carcinogenic metabolites.

Generally, compositions of the present invention include iron-polydextrose complexes characterized by one or more of various features. In certain embodiments, the complex is characterized by either or both of the following structures:

$(FeOOH).(C_6H_{12}O_5).(NaOH).(NaCl).(H_2O)$      I.

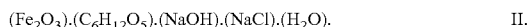

$(Fe_2O_3).(C_6H_{12}O_5).(NaOH).(NaCl).(H_2O).$      II.

Further, compositions of the present invention include iron-polydextrose complexes characterized by one or more of various features. In certain embodiments, the complex is characterized by either or both of the following structures:

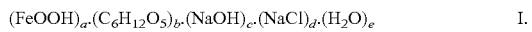

$(FeOOH)_a.(C_6H_{12}O_5)_b.(NaOH)_c.(NaCl)_d.(H_2O)_e$      I.

$(Fe_2O_3)_v.(C_6H_{12}O_5)_w.(NaOH)_x.(NaCl)_y.(H_2O)_z.$      II.

Such structures and their particular features indicate various properties defining the complexes of the present invention. First, it is currently believed that the presence of the $C_6H_{12}O_5$ moiety (as shown in FIG. 1) clearly indicates the presence of polydextrose in the finished composition.

Regarding structure I, generally: a is from about 0.8 to about 1.2; and/or b is from about 0.15 to about 0.3; and/or c is from about 0.0 to about 0.2; and/or d is from about 0.0 to about 0.2; and/or e is from about 0.2 to about 1.0; and/or the structure I components of the complex have a chloride content of from about 0% to about 4%, as determined by elemental analysis; and/or the structure I components of the complex have an iron content of from about 25% to about 50%, as determined by elemental analysis; and/or the structure I components of the complex have a sodium content of from about 0% to about 5%, as determined by elemental analysis; and/or the structure I components of the complex have an oxygen content of from about 35% to about 45%, as determined by elemental analysis.

Regarding structure II, generally: v is from about 0.4 to about 0.6; and/or w is from about 0.18 to about 0.25; and/or x is from about 0.0 to about 0.2; and/or y is from about 0.0 to about 0.2; and/or z is from about 0.2 to about 1.0; and/or the structure II components of the complex have a chloride content of from about 0% to about 4%, as determined by elemental analysis; and/or the structure II components of the complex have an iron content of from about 25% to about 50%, as determined by elemental analysis; and/or the structure II components of the complex have a sodium content of from about 0% to about 5%, as determined by elemental analysis; and/or the structure II components of the complex have an oxygen content of from about 35% to about 45%, as determined by elemental analysis.

These and additional features of the complexes of the present invention that may be determined by elemental analysis define the complexes of the present invention and indicate advantageous features. In particular, the carbon content, iron content, and/or ratio of carbon to iron content may effectively define the complexes of the present invention.

Generally, complexes of the present invention have carbon content, as determined by elemental analysis, of at least about 3%, at least about 5%, or of at least about 7%. Overall, the carbon content of the complex may range from about 3% to about 20%, from about 5% to about 15%, or from about 7% to about 13%.

In certain embodiments, the carbon content of the complex is at least about 8%, at least about 9%, at least about 10%, or at least about 11%. Generally, higher carbon contents of the complexes of the present invention are currently believed to indicate the presence of polydextrose, which by its polymeric nature incorporates a higher proportion of sugars and consequently a higher proportion of the sugar constituent carbon as compared to PIC complexes. Higher carbon content as compared to complexes of the prior art is not required in accordance with the present invention. For example, certain other iron polysaccharide complexes (e.g., iron sucrose or iron dextrose complexes) may contain similar or even higher carbon content than the complexes of the present invention. But it is currently believed that the presence of polydextrose results in formation of iron-polydextrose complexes having relatively high carbon content generally and/or in terms of the relative proportion of carbon to iron as compared to certain iron-polysaccharide complexes, in particular PIC complexes.

Typically, the iron content of the complex is at least about 30%, at least about 35%, at least about 40%, or at least about 45%. Overall, the iron content of the composition may be from about 30% to about 50%, from about 40% to about 50%, or from about 42% to about 48%.

Iron contents of the complexes of the present invention generally may be at or near those of prior iron complexes. Slight increases of iron content may be observed, but such an increase is not required in accordance with the present invention.

The iron content as compared to the carbon content is currently believed to indicate the presence of polydextrose. Generally, the ratio of C:Fe, as determined by elemental analysis, is at least about 0.1:1, at least about 0.15:1, at least about 0.2:1; at least about 0.25:1, or at least about 0.3:1. Overall the complexes of the present invention typically exhibit a ratio of C:Fe of from about 0.1:1 to about 0.7:1, or from about 0.2:1 to about 0.5:1.

It is further currently believed that certain surface features of the complexes of the present invention are indicative of the presence of polydextrose. Generally, the term "surface" in accordance with this discussion is to be understood to refer to the outermost regions of the complexes of the present invention with the iron oxyhydroxide-containing core generally constituting the innermost regions. Surface analysis techniques have identified relatively high carbon content at the surface of the iron-polydextrose complexes of the present invention and likewise relatively low iron content at the complex surface. Such techniques include energy dispersive X-ray spectroscopy (EDS), Fourier Transform Infrared Spectroscopy (FTIR) analysis, and Raman Spectroscopy as described elsewhere herein.

As detailed above, complexes of the present invention include an iron oxyhydroxide-containing core. This core is currently believed to be bound to and surrounded by polydextrose molecules therefore defining an outer region of the complex rich in polydextrose molecules. This outer region is generally rich in carbon as compared to iron.

Additionally or alternatively, this polydextrose-rich outer surface of the complex may be indicated by the results of energy dispersive X-ray spectroscopy (EDS), with the complex exhibiting a signal corresponding to a surface carbon content of at least 25% and a surface iron content of less than 60%. Further additionally or alternatively, when analyzed by Fourier Transform Infrared Spectroscopy (FTIR) analysis, the complex may exhibit (i) an absorption band at approximately 1600 $cm^{-1}$ having an intensity of at least 30% lower as compared to a corresponding complex comprising sucrose instead of polydextrose; and (ii) an absorption band at approximately 1100 $cm^{-1}$ having an intensity at least 30% higher as compared to a corresponding complex comprising sucrose instead of polydextrose. The complex of the present invention may also, when analyzed by Raman Spectroscopy (e.g., as described herein in Example 13) be characterized by a Raman Scanning Intensity of less than 150 over a scanning region of from about 1200 $cm^{-1}$ to 1900 $cm^{-1}$.

Particulate Iron-Polysaccharide Complex Compositions

Generally, the inventive complexes include iron (III) ions in some form bonded to, or complexed with the polysaccharide polydextrose. The method of preparing the complexes as detailed herein is conducted in the aqueous phase, thereby providing the desired complex within a mixture or slurry including the inventive complex. This slurry itself may be considered a composition of the present invention. For example, a slurry having a moisture content in the range of from about 30 weight % to about 95 weight % and including certain impurities may be the composition including the inventive complexes of the present invention. In such instances various features of the particulate compositions of the present invention apply as well including, for example, iron content, carbon content and/or carbon:iron ratio, as determined by elemental analysis.

In various preferred embodiments, the composition of the present invention is a particulate composition that has been prepared by methods detailed herein that include, for example, one or more drying, filtering (e.g., ultrafiltration), and/or lyophilizing steps. Particulate compositions of the present invention are suitable for use in various applications, including for use in preparing tablets, capsules, and also for use in intravenous (IV) formulations.

Typically, a dried particulate composition of the present invention has a moisture content of no more than about 10 weight %, or from about 4 weight % to about 8 weight %. Such products are suitable for formulating into, for example, a tablet or a capsule.

Overall, to aid in subsequent processing relatively consistent particle size distribution generally is desired. Such desired particle size distribution may be expressed by a certain minimum percentage (on a weight basis) of particles within a range of particle size, including a relatively high proportion of particles (by weight) within a certain narrow range of particle size. Overall, particles within a range from 1 to 50 μm are preferred with advantageous properties believe to be provided by a significant fraction of particles below 20 μm and/or near 10 μm. Generally, the particulates range in color from a dark brown to black colored powder based on the particle size. Generally, below 15 microns, the particles tend to take on a brown color, while above 15 microns the particles tend to take on a black color. Variation in the product particle size can affect the compression characteristics of the product resulting in tablets, wafers, or lozenges not meeting their desired physical characteristics, e.g., hardness, thickness, friability, dissolution, etc. The relatively low particle size for particulates of the present invention provides rapid dissolution of the particles and also provides certain processing benefits, including improved processing during bead coating and ease in in final product manufacturing.

Generally, a particulate composition of the present invention has a particle size distribution such that at least about 50% (weight basis) of the particles have a particle size in a range of from about 0.1 μm to about 50 μm, and more generally such that at least about 50% (weight basis) of the particles have a particle size in a range of from about 1 μm to about 50 μm.

Typically, the particulate composition has a particle size distribution such that at least about 50% (weight basis), at least about 60% (weight basis), at least about 70% (weight basis), at least about 80% (weight basis), or at least about 90% (weight basis) of the particles have a particle size in a range of from about 1 μm to about 30 μm.

In certain embodiments, the particulate composition has a particle size distribution such that at least about 50% (weight basis) of the particles have a particle size in a range of from about 5 μm to about 30 μm, from about 5 μm to about 25 μm, from about 5 μm to about 20 μm, or from about 10 μm to about 20 μm.

In other embodiments, the particulate has a particle size distribution such that at least about 60% (weight basis), at least about 70% (weight basis), at least about 80% (weight basis), or at least about 90% (weight basis) of the particles have a particle size in a range of from about 10 μm to about 20 μm.

Dried, particulate compositions of the present invention typically contain sodium chloride as a remnant of the synthesis. The presence of sodium chloride in the complex thus may indicate the presence of reaction byproducts and unreacted polydextrose. The dried particulate of the present invention typically contains no more than about 3.5 weight % sodium chloride.

Generally, the measured pH of the iron polydextrose particulate is from about 9 to about 12. The measured free alkali pH is not more than about 9.0.

The amount of elemental iron in the particulate is generally from about 25 weight % to about 50 weight %, from about 35 weight % to about 48 weight %, or from about 40 weight % to about 48 weight % of the composition. Typically, the amount of free ferric ion is not more than about 0.5 weight %.

Typically, particulate compositions of the present invention have water solubility in neutral pH water of at least about 0.1 mg/ml, at least about 0.5 mg/ml, at least about 1 mg/ml, or at least about 5 mg/ml.

In various embodiments, the solubility of the particulate is greater than 1 mg/mL in a pH 2.5 solution. The solubility of the particulate is highest in high and low pH solutions. When the particulates are added to water the pH increases, due to the basic nature of the complex, thus increasing the solubility of the particulate in water.

Preferably, the resulting particulates do not promote and in fact hinder the growth of microorganisms. For example, particulates have a total microbial count of not more than about 1000 cfu/g (and typically significantly lower) and a yeast and mold count of not more than 100 cfu/g (and typically significantly lower). Additionally, tests for *Escherichia coli*, various *Salmonella* species, and *Staphylococcus aureus* are negative. The resulting moisture content contributes to achieving a low microbial count.

Methods for Preparing the Iron-Polysaccharide Complex

Generally, the compositions of the present invention are prepared utilizing an aqueous reaction medium including a source of the iron (III) ions and the polysaccharide (polydextrose). An intermediate portion of the process is formation of the Fe(III)oxyhydroxide, which is facilitated by adding a source of hydroxide ions into the aqueous reaction medium.

Generally, any commercially available grade of polydextrose may be utilized in accordance with the present invention, pharmaceutical grade and food grade. Food and pharmaceutical grade polydextrose are both manufactured in accordance with current good manufacturing practices. The difference between the two grades is the purification required before the final product(s) is/are achieved. Food grade polydextrose contains slightly higher amounts of impurities as compared to pharmaceutical grade. However, food grade polydextrose is more readily available and involves lower cost, while nonetheless providing a suitable finished product. Using pharmaceutical grade polydextrose may provide advantages in terms of impurity profile. In any event, a suitable source can be selected to suit the requirements of the particular application.

The Fe(III) oxyhydroxide alone exhibits relatively low water solubility, but once the Fe(III) oxyhydroxide intermediate has reacted or complexed with the polydextrose the product is readily soluble in water. Thus, water solubility of the complex specified elsewhere herein is not only a desired property of the final product, but is also indicative of an efficient preparation method.

Typically, the source of hydroxide ions introduced into the aqueous reaction medium for formation of Fe(III)-oxyhydroxide (ferric oxyhydroxide) is selected from the group consisting of sodium hydroxide, potassium hydroxide, ammonium hydroxide, and combinations thereof. The preferred source of hydroxide ions is sodium hydroxide.

The purpose of introducing the source of hydroxide ions is formation of Fe(III)-oxyhydroxide (ferric oxyhydroxide), which readily and typically occurs at a pH of less than about 5, less than about 4, or less than about 3. Generally, the pH during formation of Fe(III)-oxyhydroxide (ferric oxyhydroxide) is from about 1 to about 6, from about 2 to about 5, or from about 3 to about 4.

The source of hydroxide ions introduced into the aqueous reaction medium is typically added as a 50 weight % solution and in a proportion that provides a weight ratio of hydroxide ions to Fe(III) at about 2.5:1.

The temperature of the aqueous reaction medium during formation of Fe(III)-oxyhydroxide is typically from about 15° C. to about 75° C., from about 20° C. to about 70° C., or from about 20° C. to about 60° C.

Generally, the aqueous reaction medium is agitated during formation of Fe(III)-oxyhydroxide, typically by an impeller operated at a rate of from about 100 to about 300 revolutions per minute (RPM).

After formation of the Fe(III)oxyhydroxide, the goal is formation of the iron-polysaccharide (polydextrose) complex. As detailed elsewhere herein, it is currently believed that this complex includes Fe(III) oxyhydroxide bonded or complexed with the polydextrose, in particular hydroxyl and oxo sites on the polydextrose. The complex may also include Fe(III) ions bonded or complexed directly with the polydextrose. It is to be understood that reference herein to an iron-polysaccharide (polydextrose) complex is intended to include either or both forms of iron (III) ions bonded with the polydextrose.

In any event, suitable formation of the iron-polysaccharide complex includes additional adjustment of the pH after a period of adjustment for formation of the Fe(III)oxyhydroxide. A source of hydroxide ions is typically introduced for this purpose.

This second pH adjustment for formation of the iron-polysaccharide complex occurs by virtue of the presence of and/or addition of a source of hydroxide ions. In certain embodiments, the pH may be adjusted by virtue of the source of hydroxide ions already present in the reaction mixture. Typically, however, additional source of hydroxide ions for pH adjustment to form the iron-polysaccharide complex is introduced into the reaction mixture.

Generally, a second source of hydroxide ions is selected from the group consisting of sodium hydroxide, potassium hydroxide, and combinations thereof. Typically, this second source of hydroxide ions is sodium hydroxide, and more typically a 50 weight % solution of sodium hydroxide. Generally, the same source of hydroxide ions is used for each addition.

Alternatively, a source of hydroxide ions, preferably sodium hydroxide, is introduced into the aqueous reaction medium as one continuous addition that continues following the addition of ferric chloride and polydextrose. During this continuous addition of sodium hydroxide, Fe(III)-oxyhydroxide and the Fe(III)oxyhydroxide-polydextrose complex are formed.

The addition or presence of the source of hydroxide ions for formation of the iron-polysaccharide complex provides a pH of the aqueous reaction medium of at least about 4, at least about 5, or at least about 6. Typically, the pH of the aqueous reaction medium for this purpose is from about 1 to about 13, from about 5 to about 12, or from about 6 to about 12.

During preparation of the iron polydextrose complex, sorbitol can be added to the aqueous reaction medium to increase the cross linking between Fe(III)-oxyhydroxide and polydextrose. Generally, sorbitol is introduced into the aqueous reaction medium to provide a sorbitol to polydextrose weight ratio of at least 0.1:1, or at least about 0.25:1. Typically, the weight ratio of sorbitol to polydextrose is from about 0.1:1 to about 0.5:1. When utilized, typically sorbitol is introduced along with the polydextrose. It is to be understood, however, that sorbitol is not required for preparation of an effective composition.

The temperature of the aqueous reaction medium during formation of the iron-polysaccharide complex may at one or more points in the process be from about 50° C. to about 120° C., from about 60° C. to about 110° C., or from about 70° C. to about 100° C.

If necessary, the aqueous reaction mixture is allowed to cool to a temperature of less than about 70° C., less than about 60° C., or less than about 50° C., thereby forming an iron-polydextrose product slurry.

Operating according to the preceding description provides a reaction tank that conduces and provides formation of the iron-polysaccharide complex. That is, the complex itself is formed under the conditions provided in this reaction tank and a mixture or slurry from this reaction mixture may be the desired final product, or the desired product may be provided upon further purification.

Generally, in accordance with the present invention it has been observed that use of polydextrose results in particular temperature profiles during complex preparation. In particular, the use of polydextrose is believed to result in lower overall temperatures and/or reduced increases in temperature during preparation of the complex (e.g., over the time period from introduction of the first source of hydroxide ions to the formation of the complex). For example, it has been observed that after the second addition of hydroxide ions that a temperatures no greater than about 100° C., no greater than about 95° C., or no greater than about 90° C. (e.g., temperatures of about 85° C., or lower) are achieved within the reaction mixture. Additionally or alternatively, it has been observed that the temperature of the reaction medium does not increase more than about 40° C., more than about 35° C., or no more than about 30° C. from addition of the first source of hydroxide ions to completion of the mixing following introduction of the second source of hydroxide ions. These temperature phenomena are currently believed to be due to the presence of polydextrose and the concomitant absence of constituent sugars that may undergo Maillard's reaction and/or caramelization and therefore result in a temperature spike to above the listed limits based on the exothermic nature of these reactions. Avoiding a temperature spike results in reduced downstream cooling requirements.

Typically, the aqueous reaction medium at this stage (e.g., an intermediate iron-polydextrose product slurry) has a moisture content of at least about 30 weight %, at least about 40 weight %, from about 30 to about 95 weight %, or from about 40 to about 95 weight %. This slurry may be a product of the invention itself and formulated into a liquid formulation. Alternatively, the slurry is further processed by one or more drying operations to provide a particulate composition of the present invention.

Typically, the source of Fe(III) ions introduced into the reaction mixture is selected from the group consisting of ferric chloride, ferric sulfate, ferric citrate, ferric nitrate, ferric ammonium sulfate, ferric nitrate, and combinations thereof. Preferably, the source of Fe(III) ions is ferric chloride.

Generally, the weight ratio of Fe(III) ions to polydextrose introduced into the aqueous reaction medium is at least about 0.1:1, at least about 0.2:1, or at least about 0.3:1. Typically, the weight ratio of Fe(III) ions to polydextrose introduced into the aqueous reaction medium is from about 0.1:1 to about 5:1, from about 0.3:1 to about 3:1, or from about 0.5:1 to about 2:1.

To promote dispersion and preferably dissolution of the polydextrose throughout the liquid medium, the resulting mixture is generally heated to about 28° C. and agitated. The mixture is agitated at about 300 revolutions per minute (rpm) utilizing a suitable apparatus known in the art to provide dispersion of all components.

Following formation of the iron(III)-polydextrose complex within the aqueous reaction medium, the resulting mixture or slurry is subjected to various processing steps in order to provide the desired final product(s).

Typically, the slurry is subjected to a separation or filtration operation to remove water and ultimately recover a particulate product. The iron polydextrose product slurry can be purified using techniques known to those skilled in the art, e.g. ultrafiltration, chromatography, and precipitation. For ultrafiltration, membrane having a molecular weight cut off of from about 10 KDa to about 100 KDa is used. In certain embodiments precipitation is utilized to recover a particulate intermediate product.

Regardless of the precise method of recovery, the slurry is generally agitated during recovery of the particulate product therefrom. This agitation may be conducted by simple mixing.

The filtrate or precipitate recovered from the iron polydextrose product slurry can be spray dried to form a dried particulate. This can be accomplished utilizing a suitable spray drying apparatus under conditions that can readily be selected by one skilled in the art. For further product purification, the spray dried product may be passed through a 6-20 mesh screen, for delumping purposes, before being packaged. The packaging of the particulate occurs in a room supplied with HEPA filtered air. The particulates are packaged into polyethylene lined containers, e.g., drums, boxes, etc., containing desiccants.

Forms of Administration/Dosages/Methods of Treatment

Generally, polydextrose is a water-soluble bulking agent and is a randomly cross-linked (branched) glucan polymer (polysaccharide) characterized by having predominantly β-1-6 and β-1-4 linkages. Polydextrose is generally produced through acid-catalyzed condensation of saccharides alone or in the presence of sugar alcohols and is distinct from other polysaccharides. For example, polydextrose is substantially different from maltodextrin, which is obtained through the hydrolysis of starch materials and which contains a majority of α-1-4 linkages. Polydextrose also contains a relatively high non-digestible fiber content of, for example, at least about 80 weight % such as found, for example, in the commercially available LITESSE polydextrose. Non-digestible fiber is neither digested nor absorbed in the small intestine and typically increases bowel movements, stimulates colonic fermentation, reduces fasting cholesterol levels, and/or reduces post-prandial blood sugar and/or insulin levels. The proportion of non-digestible fiber present in the polydextrose may be determined, for example, by applying fresh dialyzed rat small intestine powder at 37° C. at pH 6.

In accordance with the present invention, applicants have discovered that the fact that polydextrose contains non-digestible fiber provides various advantageous features that enhance the desirability of the use of iron-polysaccharide complexes generally. As detailed above, various complexes are generally known in the art when prepared using polysaccharides other than polydextrose. In certain embodiments, the current discovery combines the non-digestible fiber aspect of polydextrose with the known iron-supplementation for conventional iron-polydextrose complexes. For example, constipation is well-known side effect of treatment of iron-deficiency anemia. The non-digestible fiber of the polydextrose is believed to address and/or less the severity of this side-effect.

Generally, the compositions of the present invention can be formulated into any dosage form suitable for administration to a human or other mammal. The dosage form may generally comprise any biologically acceptable excipient known in the art. Generally speaking, it is currently believed that various features of the particulate compositions of the present invention (e.g., flowability, narrow particle size distribution) allow for ease in preparation of iron supplements and also readily allow formulating the compositions of the present invention with other components (e.g., other nutritional supplements such as vitamins and minerals).

In some embodiments, the compositions of the present invention are formulated into a solid oral dosage form. Non-limiting examples of solid oral dosage forms include tablets, soft chewable tablets, hard or soft gelatin capsules, pills, pellets, and troches and/or lozenges.

In various embodiments of the present invention, tablets are a preferred dosage form. Tablets according to the present invention may be prepared using any conventional tableting methods known in the art, including by granulation, compression, or molding methods. In a preferred embodiment, the tablet has a hardness of at least about 5 kilopascals (kPa).

The compositions of the present invention may also be formulated as liquid compositions, either for oral ingestion or as an injectable medium. Non-limiting examples of liquid compositions suitable for oral ingestion include elixirs, solutions, suspensions and syrups. Compositions of the present invention may also be incorporated into intravenous (IV) formulations. Such IV formulations may incorporate a particulate product described above. Alternatively, product slurry of the present invention may be readily formulated into such a liquid formulation. Some purification of this slurry is typically undertaken, but processing all the way to a dried, pure particulate product is not required in all such embodiments.

Generally, the compositions of the present invention are iron supplements, and may also be considered as a fiber supplement by virtue of the presence of polydextrose.

In certain embodiments, additional vitamins and/or minerals may be introduced into a composition of the present invention to also generally provide a nutritional supplement in addition to the iron and fiber supplement.

The vitamins and/or minerals may be selected from the group consisting of potassium, calcium, copper, magnesium, zinc, folic acid (folate—vitamin B-9), vitamin B-12, vitamin D, vitamin A, flavonoids, vitamin C, manganese, lutein, zeaxanthin, lutein-zeaxanthin, beta carotene, quercetin, phenolic compounds, lipoic acid, taurine, fish oil, anthocyanosides, and combinations thereof.

Dosage forms (e.g., tablets) in accordance with the present invention may be formulated as an iron supplement including a suitable amount of iron plus additional components to provide a complete nutritional supplement. These nutritional supplements may include, for example, the following components (based on daily dosage): approximately 1 to 3 gm potassium, and/or approximately 600 to 1500 mg calcium, and/or approximately 300 to 1500 mg vitamin B-12, and/or approximately 30 to 90 mg iron, and/or approximately 1 to 3 mg copper, and/or approximately 200 to 2400 IU vitamin D, and/or approximately 2000 to 6000 IU vitamin A, and/or approximately 500 to 1500 mg flavonoids. Certain compositions of the present invention may incorporate folic acid (folate) at a concentration of from about 0.4 to about 5 mg.

Dosage forms in accordance with the present invention may also be formulated with a source of protein, comprising at least one protein selected from the group consisting of whey protein extract, whey protein isolate, whey protein hydroxylate, whey protein concentrate, soy isolate, and casein. For example, compositions may be formulated that provide a daily dose of from about 5 to about 80 gm, a daily dose of from about 30 to about 70 gm, or a daily dose of about 50 gm.

Compositions of the present invention may be designed for administration parenterally. Parenteral administration of the composition can comprise intravenous or intramuscular. Intravenous administration can be delivered as a bolus or preferably as an infusion. For example, the single unit dose of the composition can be intravenously infused at a concentration of about 1000 mg elemental iron in about 200 mL to about 300 mL of diluent. The composition can be administered intravenously as a bolus. For example, the composition can be injected as a bolus at a concentration of about 1000 mg elemental iron in about 200 mL to about 300 mL of diluent, preferably about 200 mL of diluent. The composition can be administered as an intramuscular infusion at a concentration, for example, at about 1000 mg elemental iron in about 200 mL to about 300 mL of diluent, preferably about 200 mL of diluent. If administered as an infusion, the complex can be diluted with sterile saline. Additionally, the complex can be intravenously injected as a bolus without dilution.

Generally, the total iron dosage will depend on the iron deficit of the patient. One skilled in the art can tailor the total iron dose required for the subject while avoiding iron overload.

Administration of the iron polydextrose complex can occur as a one-time delivery of a single unit dose or over the course of treatment involving delivery of multiple single unit doses.

In various embodiments, the present methods can be used to treat anemia. The anemia can be a result of iron deficiency anemia, such as that associated with chronic blood loss, acute blood loss, pregnancy, childhood development, psychomotor and cognitive development in children, breath holding spells, heavy uterine bleeding, and the like. In some embodiments, the anemia is due to impaired iron absorption or poor nutrition, such as anemia associated with Crohn's disease, gastric surgery, ingestion of drug products that inhibit iron absorption, and chronic use of calcium. In various embodiments, the method treats restless leg syndrome, blood donation, Parkinson's disease, hair loss, or attention deficit disorder.

In certain preferred embodiments, the iron supplementation is for a patient suffering from this condition by virtue of treatment for Type-2 diabetes.

Compositions of the present invention can be utilized as fiber supplements without having to be formulated with additional fiber containing products. As described above, polydextrose is considered to have 80% fiber content. Therefore, any supplement formulated with the present product will contain fiber. Additionally, the compositions of the present invention can be used to treat iron deficient anemia in type-2 diabetic patients. The polydextrose within the composition has a low glycemic index which will case a graduate rise in blood glucose levels and limit spikes in insulin levels.

Having described the invention in detail, it will be apparent that modifications and variations are possible without departing from the scope of the invention defined in the appended claims.

EXAMPLES

The following non-limiting examples are provided to further illustrate the present invention.

Example 1

An iron-polysaccharide complex was prepared as detailed herein. The reaction resulted in a dark solution that was stable to precipitation and phase separation for more than 4 days. The same reaction process with only ferric chloride produced a brown solution that quickly precipitated out of solution. Other sugars tested (xylitol, corn syrup, sorbitol, maltose) produced mixtures that quickly separated into at least two phases indicating a very heterogeneous reaction with multiple end products.

These results indicated greatest stability for the mixture prepared using ferric chloride and polydextrose.

The mixture of ferric chloride-polydextrose complex was then precipitated with ethanol, filtered and rinsed with an ethanol/deionized water mixture and dried in the vacuum oven. The Fe content of the resulting solid was determined to be approximately 36 weight %.

Example 2

Following are details of spray drying that can be utilized to process iron-polydextrose complexes prepared in accordance with the present invention, including Example 1 above and the additional working examples provided herein.

This procedure may be applied to an R&D GEA/Niro Spray Dryer (Moble Minor) operated in Nozzle, Co-Current mode using a nozzle 1.0 mm in size.

TABLE 1

| Inlet Temp. (° C.) | Outlet Temp. (° C.) | Air Velocity (mm $H_2O$) | Atm Air Press/Flow Nozzle (Bar/Flow) | Spray Rate (Pump Set) (g/min) | Chamber Pressure (mmWS) | Product Moisture (%) |
|---|---|---|---|---|---|---|
| 200 | 72 | 22-24 | 5.4/78 psi | 14@40 gm/min | −180 | N/A |

During operation a stir bar is placed in the bottle of slurry and set on a stir/mixer. A peristaltic pump with silicone MASTERFLEX tubing #L/S17 was used to deliver the slurry to the spray nozzle. The spray process proceeds smoothly and the product is swept out of the chamber easily. Oversized particles were collected at the bottom of the chamber and the desired size particles with a mean diameter of 6.4 μm are collected from the cyclone bottle.

Example 3

The following example details preparation of an iron-polydextrose complex based on the composition of the present invention.

Materials/Equipment:
400.0 ml Deionized $H_2O$
114.0 gm LITESSE Polydextrose, Danisco
376.5 gm Iron (III) Chloride Solution, Sigma-Aldrich
300.0 gm Sodium Hydroxide 50% Solution, Sigma-Aldrich
2 L PYREX beaker with WATLOW silicone heat wrap
STACO 120V VARIAC VWR Power Max overhead mixer with stainless steel 2.5" 3-blade impeller
NUOVA 10" Hot plate
Koch Membrane Systems Demo Filter Kit with PM-100 filter The water was weighed into a 2 L heat wrapped PYREX beaker set on the hot plate with overhead mixer and impeller. The polydextrose was added and stirred until dissolved, for approximately 5-10 minutes. This solution was at a temperature of approximately 28° C. The ferric chloride was then slowly added while mixing at a speed of approximately 300 rpm. This mixing time was at least 5 minutes and the resulting temperature of the mixture after this addition was approximately 33° C. 150.0 gm of the sodium hydroxide 50% solution was weighed into a 200 ml PYREX beaker and slowly added to the mixture over an addition time of approximately 2 minutes. Total mixing time was greater than 15 minutes with the temperature at approximately 73° C. following this addition. There was no obvious change in the torque reading of 21.6-22.0 on the mixer seen after this addition.

The remaining 150.0 gm sodium hydroxide 50% solution was then slowly added. After adding about 40.0 gm of this remaining solution, the mixture in the beaker thickened and the torque reading on the mixer increased to 34.6 and the mixer speed was increased to 450 rpm as the addition continued. Upon further mixing, the mixture decreased in viscosity and the speed was reduced to 350 rpm. A temperature reading of 82° C. was achieved. The VARIAC mixer was turned on to 45% and the hot plate to 9 on the dial setting. The beaker was wrapped and covered with aluminum foil and mixed at 350 rpm for 3 hours with the temperature held between 85-90° C.

After this time the heat was turned off and the hot plate removed but mixing continued. When the temperature of the mixture reached approximately 50° C. the stirrer was removed and the mixture poured into a clean, tared 1 L PYREX beaker (752 ml/612.0 gm). A portion was taken and subjected to ultrafiltration as follows and another unfiltered sample was placed in a 20 ml sample bottle for later observation. Filter apparatus included the PM-100 lab test filter and 3 L deionized $H_2O$ measured into a separate 4 L beaker to use in the process. The beaker containing the unfiltered material was placed on a scale next to the filter apparatus and the inlet and outlet hoses inserted. The pump was started and pressure adjusted to approximately 20-30 psi. The waste effluent was collected in a 4 L beaker. When the level in the product beaker was reduced to about 500 ml, an additional 500 ml deionized water was added and this was stirred gently. This process step was continued until all 3 L water had been used. The filtration was further run until the level in the beaker was reduced to 300 ml/358.0 gm. Total filtration time was approximately 3 hours.

About 20 ml of this concentrate was placed in a plastic weigh boat and set in the vacuum oven to dry overnight. After drying, the sample was milled and placed in a labeled sample jar for assay testing for iron content. Iron content was determined to be 37.4%.

The remainder of the concentrate was poured into a 500 ml jar with lid for storage. The concentrate was subjected to spray drying under the conditions set forth above: Amount Produced=Chamber: 3.2 gm; Cyclone=19.2 gm; Total=22.4 gm. A stir bar was placed in the bottle of slurry and set on a stir/mixer. A small amount of deionized water was added to thin down the slurry which was very vicious. A peristaltic pump with silicone MASTERFLEX tubing #L/S17 was used to deliver the slurry to the spray nozzle. The spray process went smoothly and the product swept out of the chamber easily. Oversized particles were collected at the bottom of the chamber and the desired size particles with a mean diameter of 8.7 μm from the Cyclone bottle.

Figure 3:
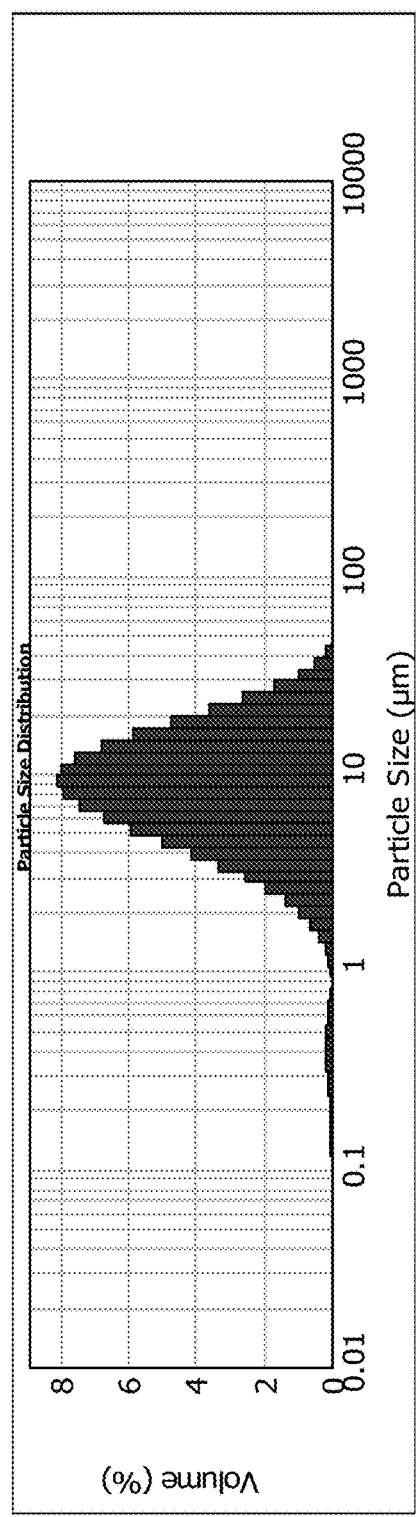

The resulting dried particulate was subjected to particle size analysis with the results shown in FIGS. 3 and 4.

Example 4

Another complex batch was prepared following the procedure detailed in Example 3, but using half the amount of polydextrose and adjusting the amounts of water, iron(III) chloride, and sodium hydroxide. The iron content assay of this complex after ultrafiltration and milling was 47% iron content.

Materials/Equipment:
533.0 ml Deionized $H_2O$
76.0 gm LITESSE Polydextrose, Danisco
502.0 gm Iron (III) Chloride Solution, Sigma-Aldrich
300.0 gm Sodium Hydroxide 50% Solution, Sigma-Aldrich
2 L PYREX beaker with WATLOW silicone heat wrap
STACO 120V VARIAC VWR Power Max overhead mixer with stainless steel 2.5" 3-blade impeller
NUOVA 10" Hot plate
Koch Membrane Systems Demo Filter Kit with PM-100 filter The concentrate was subjected to spray drying under the conditions set forth above: Amount Produced=Chamber: 5.8 gm; Cyclone=28.7 gm; Total=35.4 gm. A stir bar was placed in the bottle of slurry and set on a stir/mixer. A small amount of deionized water was added to thin down the slurry which was very vicious. A peristaltic pump with silicone MASTERFLEX tubing #L/S17 was used to deliver the slurry to the spray nozzle. The spray process went smoothly and the product swept out of the chamber easily. Oversized particles were collected at the bottom of the chamber and the desired size particles with a mean diameter of 11 μm from the Cyclone bottle.

Figure 5:
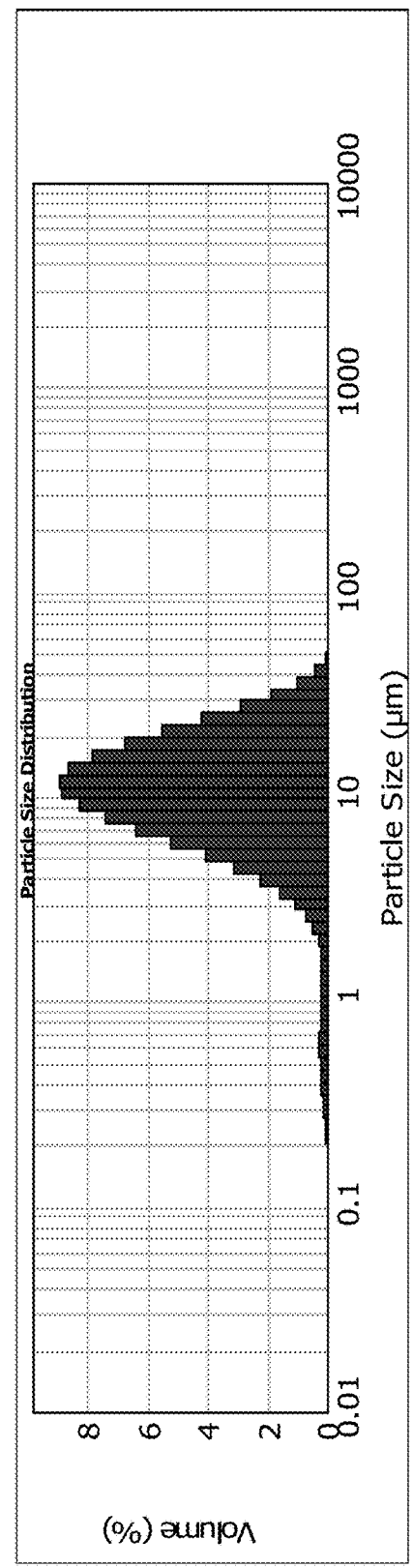

The resulting dried particulate was subjected to particle size analysis with the results shown in FIGS. 5 and 6.

Example 5

Another complex batch was prepared following the procedure detailed in Example 3, but again adjusting the amount of polydextrose and adjusting the amounts of water, iron(III) chloride, and sodium hydroxide. The iron content assay of this complex after ultrafiltration and milling was 44.7% iron content.

Materials/Equipment:
533.0 ml Deionized $H_2O$
38.0 gm LITESSE Polydextrose, Danisco
502.0 gm Iron (III) Chloride Solution, Sigma-Aldrich
400.0 gm Sodium Hydroxide 50% Solution, Sigma-Aldrich
2 L PYREX beaker with WATLOW silicone heat wrap
STACO 120V VARIAC VWR Power Max overhead mixer with stainless steel 2.5" 3-blade impeller
NUOVA 10" Hot plate
Koch Membrane Systems Demo Filter Kit w/PM-100 filter The concentrate was subjected to spray drying under the conditions set forth above: Amount Produced=Chamber: 2.4 gm; Cyclone=27.5 gm; Total=29.9 gm. A stir bar was placed in the bottle of slurry and set on a stir/mixer. A small amount of deionized water was added to thin down the slurry which was very vicious. A peristaltic pump with silicone MASTERFLEX tubing #L/S17 was used to deliver the slurry to the spray nozzle. The spray process went smoothly and the product swept out of the chamber easily. Oversized particles were collected at the bottom of the chamber and the desired size particles with a mean diameter of 10.9 μm from the Cyclone bottle.

Figure 7:
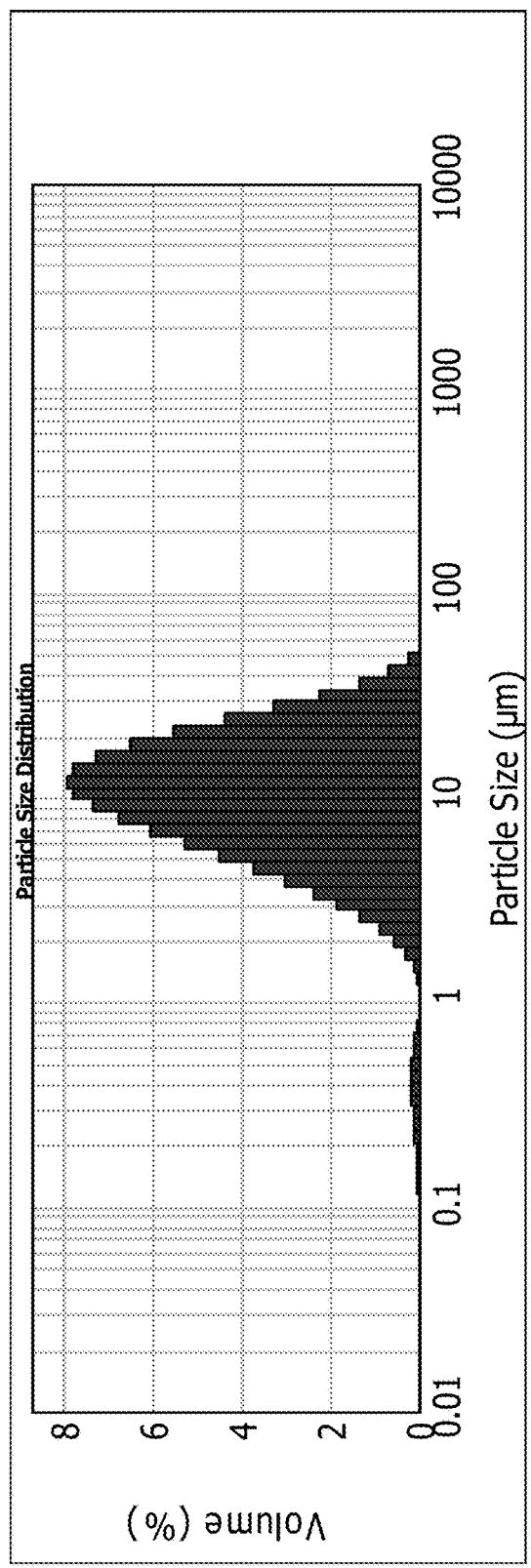

The resulting dried particulate was subjected to particle size analysis with the results shown in FIGS. 7 and 8.

Following are summaries of the formulations and results for the compositions of Examples 3-5.

TABLE 2

| Formulations Reagents | Example 3 | Example 4 Mass (gm) | Example 5 | Supplier |
| --- | --- | --- | --- | --- |
| Deionized $H_2O$ | 400.0 | 533.0 | 533.0 | PDI |
| LITESSE (polydextrose) | 114.0 | 76.0 | 38.0 | Danisco |
| $FeCl_3$ | 376.5 | 502.0 | 502.0 | Sigma-Aldrich |
| NaOH (50% solution) | 300.0 | 300.0 | 400.0 | Sigma-Aldrich |

TABLE 3

| Formulation | Inlet Temp. (° C.) | Outlet Temp. (° C.) | Air Velocity (mm H₂O) | Atm Air Press/Flow-Nozzle (Bar/Flow, psi) | Spray Rate (Pump Set) (gm/min) | Chamber Pressure (mmWS) |
|---|---|---|---|---|---|---|
| Example 3 | 200 | 72 | 22-24 | 5.4/78 psi | 14 @ 40 gm/min | −180 |
| Example 4 | 205 | 73 | 22-24 | 5.4/78 psi | 14 @ 40 gm/min | −180 |
| Example 5 | 202 | 71 | 22-24 | 5.4/78 psi | 14 @ 40 gm/min | −180 |

TABLE 4

| Formulation | Mean Particle Size (μm) | Chamber (gm) | Cyclone (gm) | Total (gm) |
|---|---|---|---|---|
| Example 3 | 8.7 | 3.2 | 19.2 | 22.4 |
| Example 4 | 11 | 5.8 | 28.7 | 34.5 |
| Example 5 | 10.9 | 2.4 | 27.5 | 29.9 |

The following table summarizes features of formulations prepared and described in Examples 3-5 and additional complexes prepared under the noted conditions.

TABLE 5

| | Ex3 | Ex4 | Ex5 | A | B | C | D | E |
|---|---|---|---|---|---|---|---|---|
| Polydextrose Ratio | 1:1 | 0.5:1 | 0.25:1 | 0.5:1 | 2:1 | 1.5:1 | 1.6:1 | 1.6:1 |
| Polydextrose per Fe (gm/gm) | 2.22 | 1.11 | 0.56 | 1.11 | 4.45 | 3.33 | 3.58 | 3.58 |
| Sorbitol to Polydextrose Ratio | 0 | 0 | 0 | 0 | 0 | 0 | 0.35 | 0.175 |
| NaCl | 0.8% | 0.5% | 0.9% | 1.9% | 2.4% | 2.0% | n/a | n/a |
| Moisture | 5.3% | 3.1% | 8.2% | 8.0% | 4.2% | 5.0% | 4.9% | 5.6% |
| pH | 11.7 | 4.7 | 10.5 | 10.5 | 11.0 | 11.5 | 11.8 | 11.8 |
| Free Alkali | 7.8 | 2.6 | 6.2 | 5.4 | 6.0 | 7.3 | n/a | n/a |
| Assay | 36.9% | 44.4% | 42.3% | 39.9% | 29.1% | 29.4% | 25.0% | 34.8% |
| Solubility (mg/mL) | 3 | 1 | 0.2 | 0.5 | 7 | 3 | 7 | 7 |
| Solubility at pH 2.5 (mg/mL) | 5 | 5 | 1 | n/a | n/a | n/a | n/a | n/a |

Figure 9:
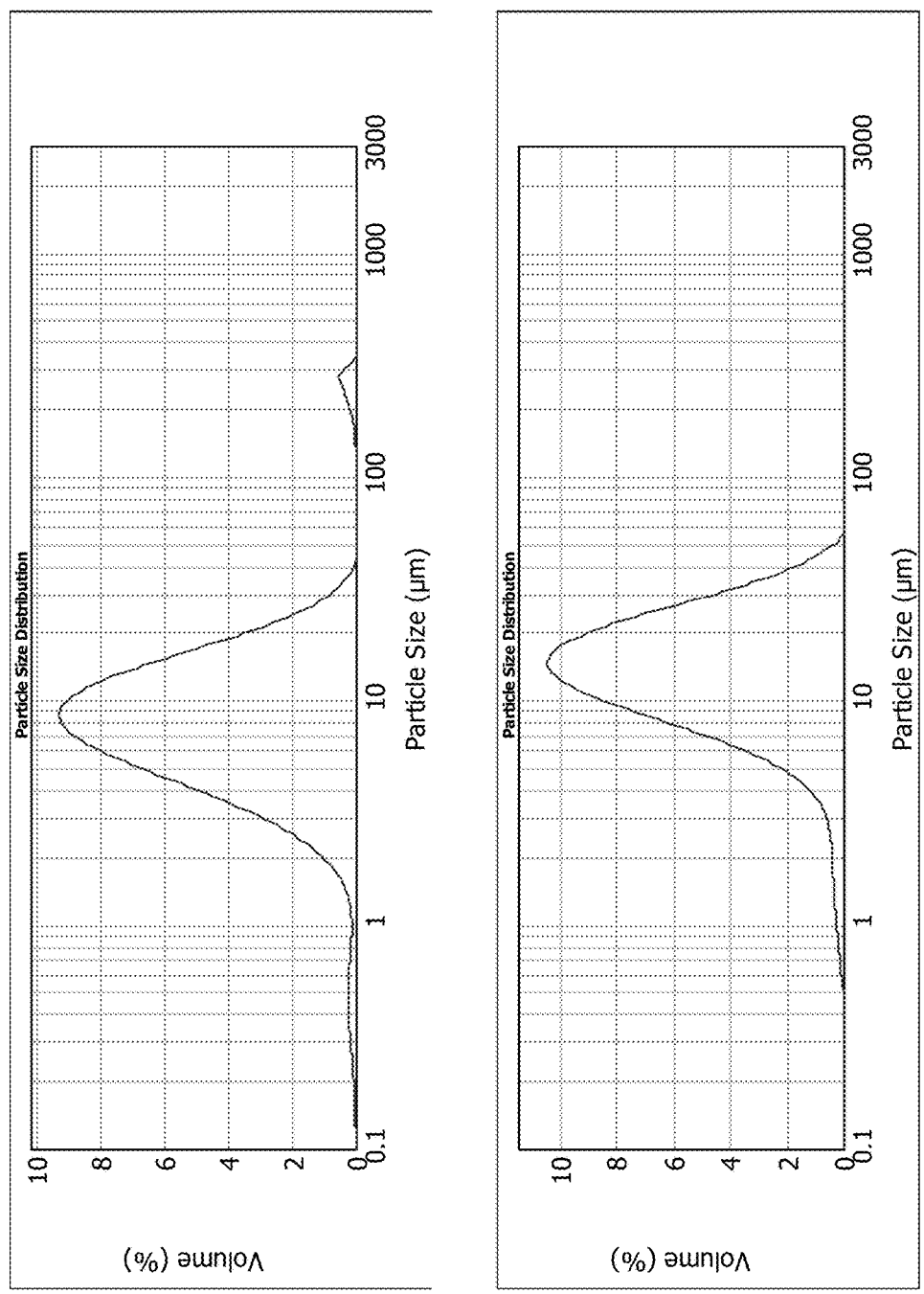

The resulting dried particulate of sample B was subjected to particle size analysis with the results show in FIG. 9.

Example 6

Two commercial scale batches of the PDIC composition of the present invention were prepared in a GMP manufacturing facility. Polydextrose replaced corn syrup utilized to make the PIC product.

Materials/Equipment:
984 kg purified H₂O
86 kg Sorbitol 70% solution
263 kg LITESSE Polydextrose 72% solution, Danisco
1130 kg Iron (III) Chloride 40% solution, Sigma-Aldrich
880 kg Sodium Hydroxide 50% solution, Sigma-Aldrich The polydextrose was weighed and added to the reaction vessel. The sorbitol solution was then added to the reaction vessel. The purified water was added and stirred for not less than 5 minutes. The ferric chloride was then slowly added and stirred for not less than 5 minutes. 450 kg of the sodium hydroxide 50% solution was weighed and slowly added to the mixture and mixed for not less than 30 minutes.

The remaining 430 kg sodium hydroxide 50% solution was then slowly added and this mixture was mixed for not less than 15 minutes. The temperature of the reaction vessel contents was maintained at not less than 70° C. for a total of 30 minutes, followed by cooling of the mixture to approximately 60° C. This mixture was then mixed for at least 1 hour.

Filtration Step

Upon completion of the chemical reaction and cooling to about 60° C., purified water or rinse water was added to the reaction tank to dilute/wash and further cool the reaction mixture to about 55° C. The suspension of PDIC in the reaction vessel was recirculated between the ultra-filtration assemblies and the mix tank to remove the sodium chloride by-product and any unreacted polydextrose and to concentrate the suspension. Filtrate from the ultrafiltration filters was drained to the process area sump, while the remainder was circulated back to the mix tank. As the product was filtered, batches of purified water were added to the mix tank automatically as the level in the mix tank dropped. After the required amount of purified water was added, the filtration continued until the remaining concentrate reached a predetermined level (700 kg to 900 kg in the mix tank and piping) and then stopped. Filtered product was pumped to a 500 gallon (316 L) stainless steel dryer feed tank.

Spray Drying

After the completion of the ultra-filtration process, the suspension is spray dried to produce a fine brown-black powder. At the completion of the filtering process, the PDIC concentrate was transferred to the spray dryer feed tank. During spray drying, the PDIC concentrate was pumped forward from the feed tank through the feed transfer pump to the atomizer disk. The PDIC concentrate was atomized and dried to the desired moisture and particle size specifications, while operating the spray dryer within the established normal operating ranges.

Samples of the batches were analyzed according to the methods described below.

Example 7

A batch of PIC was prepared in accordance with Example 6; however, polydextrose was replaced with 300 kg of corn syrup. The PIC composition was also analyzed according to the methods described below.

Example 8

Following are details for elemental analysis characterization that was performed on a PDIC complex prepared in accordance with Example 6 and a PIC complex prepared in accordance with Example 7.

Equipment:
2400 CHNS/O Series II Analyzer, PERKINELMER
OPTIMA 8300 Inductively Coupled Plasma (ICP) Atomic Emission Spectrometer, PERKINELMER Determination of carbon, hydrogen, and nitrogen content. The Series II Analyzer burns a sample in pure oxygen at 920-980° C. under static conditions to produce combustion products of $CO_2$, $H_2O$, and $N_2$. The instrument automatically separates and analyzes these products in a self-integrating, steady state thermal conductivity analyzer.

Determination of Iron and Sodium Content. Samples were nebulized and the resulting aerosol was transported to the plasma torch. Element specific emission spectra were produced by radio-frequency ICP. The spectra were dispersed by a grating spectrometer and the intensities of the emission lines were monitored by photosensitive devices.

Determination of chloride content. Chloride content was determined by suppressed ion chromatography.

Results from elemental analysis characterization are listed in the following table:

TABLE 6

| Element | PIC Composite | PDIC Composite |
|---|---|---|
| % Cl: Chloride | 1.75 | 1.88 |
| % C: Carbon | 7.35 | 11.01 |
| % Fe: Iron | 47.59 | 39.25 |
| % H: Hydrogen | 1.83 | 2.33 |
| % Na: Sodium | 3.28 | 3.82 |
| % O: Oxygen (by Difference) | 38.20 | 41.72 |

Elemental analysis results indicate the PDIC sample contains a higher sugar and sodium hydroxide percentage than the PIC sample on a unit weight basis. Additionally, it can be seen that the PDIC sample contains a higher percentage of carbon as compared to the PIC sample on a unit weight basis.

Example 9

Following are details for scanning electron microscopy (SEM) that was performed on a PDIC complex prepared as described in Example 6 and a PIC complex prepared as described in Example 7.

Equipment:
1700 Scanning Electron Microscope, AMRAY

The PDIC particulates were mounted on a conductive adhesive and placed in the microscope and analyzed using an energy dispersive X-ray spectrometer with a light element solid state detector. The samples were next removed from the microscope and sputter coated with approximately 100-200 Å of gold/palladium. The sputter coated samples were placed back into the microscope and typical SEM photographs were taken of the spheres at several magnifications.

Figure 10:
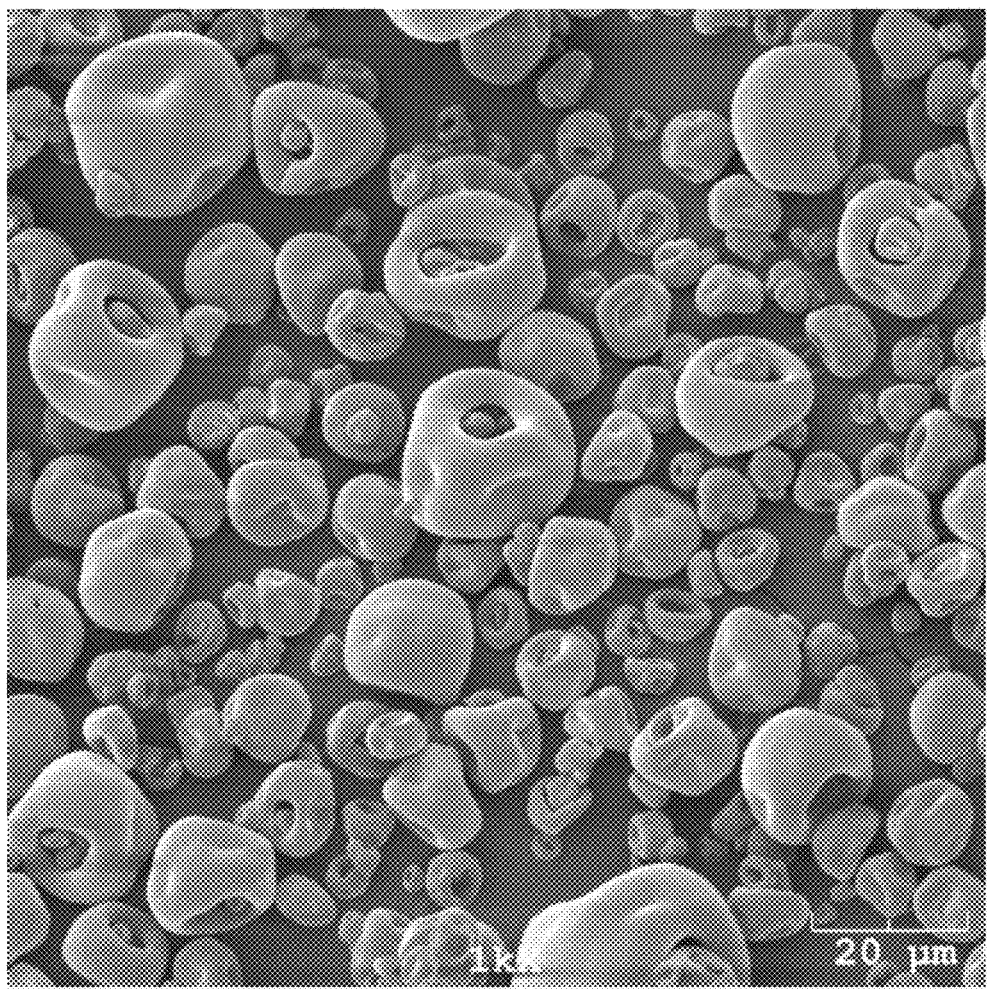
FIG. 10 shows a scanning electron microscopy (SEM) image of iron-polydextrose complex (PDIC) particulates as described in Example 9.

The SEM image provides information regarding a sample's surface topology and composition. As shown in FIG. 10 the PDIC particulates are smooth, hollow, and spherical in shape.

Example 10

Following are details for energy-dispersive X-ray spectroscopy (EDS) performed on an iron-polydextrose complex (PDIC) prepared in accordance with Example 6 and a PIC sample prepared as described in Example 7.

Composite samples were analyzed by EDS during the SEM to determine the elemental composition of the samples. An Energy Dispersive X-ray Spectrometer with a light element solid state detector was used (iXRF 550i EDS, iXRF Systems; Advanced Analysis Technologies solid state light element detector). The area under the curve for each element in the EDS graph is used to determine the percentage of each element. Note that each elemental analysis sums to 100% indicating the change in percent carbon seen in the analysis is a measured change and not subject to an error in the analysis.

Figure 11:
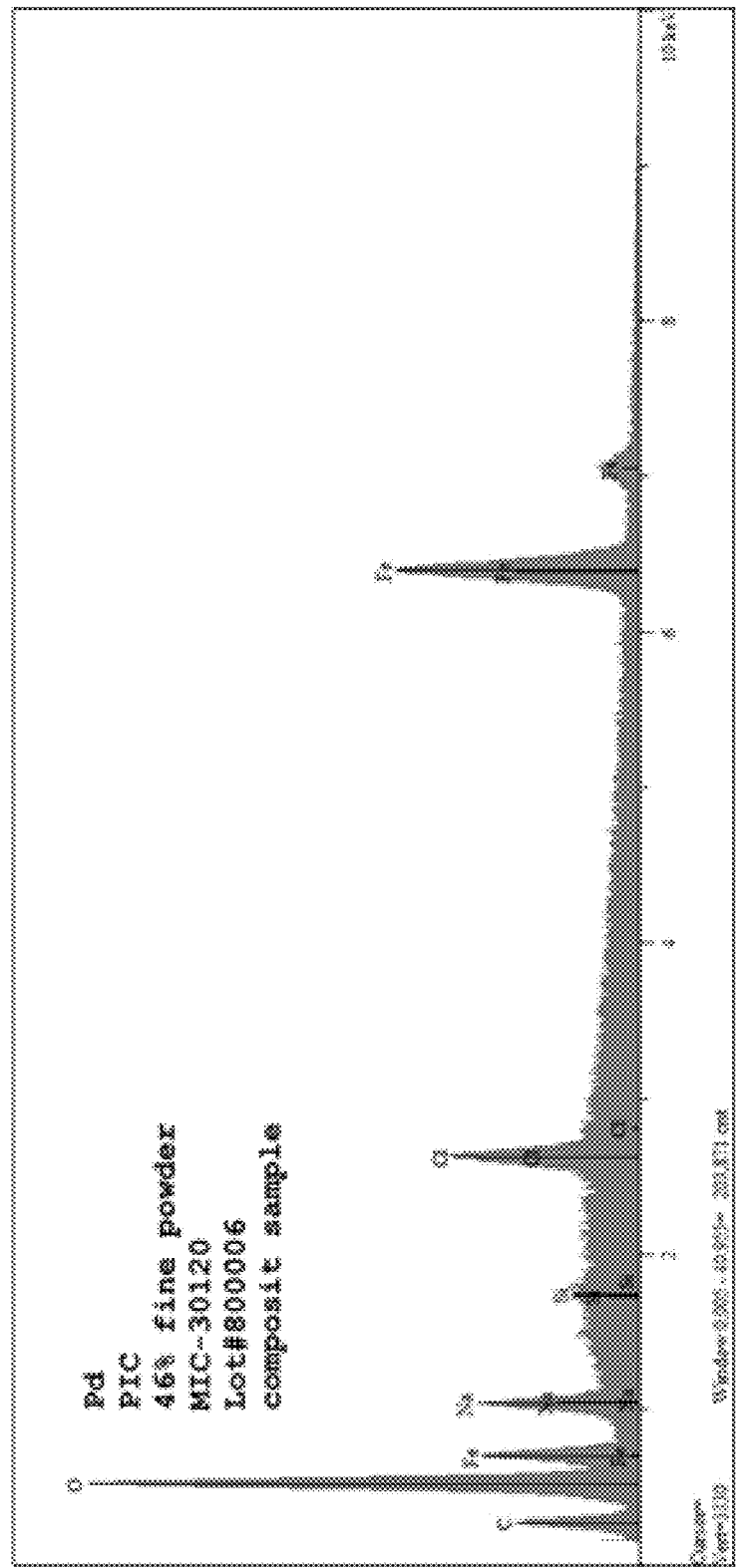
FIG. 11 shows results of Energy-dispersive X-ray spectroscopy (EDS) as described in Example 10.

Results from energy-dispersive X-ray spectroscopy are listed in the table below and shown in FIG. 11.

TABLE 7

| Element | PIC | PDIC |
|---|---|---|
| C | 20.16 | 35.8 |
| O | 8.35 | 13.5 |
| Na | 1.86 | 1.82 |
| Cl | 2.00 | 1.28 |
| Fe | 67.63 | 47.6 |

The results show the PDIC has an increase in the percentage of carbon, indicating an increase in the amount of bound sugars on the surface of the iron core as compared to PIC.

Example 11

Following are details for X-ray diffraction analysis (XRD) that was performed on an iron-polydextrose complex (PDIC) prepared in accordance with Example 6 and a PIC sample prepared as described in Example 7.

Prior to XRD analysis, powdered samples were tightly packed into sample holders with 2 mm indent using glass slides for flattening of the sample surface. The X-ray instrument used in the XRD analysis was RIGAKU MINIFLEXII automated powder diffractometer, with a generator settings of 30 kV, 15 mA and nickel-filtered CuKa (1=1.5405 Å) radiation over 2-theta range of 5-90° at a scanning rate of 0.2° $min^{-1}$. The MINIFLEXII diffractometer uses vertical goniometer type and small scintillation detector. The XRD phases present in the samples were identified by reference to the International Center for Diffraction Data (ICDD) database.

Figure 12:
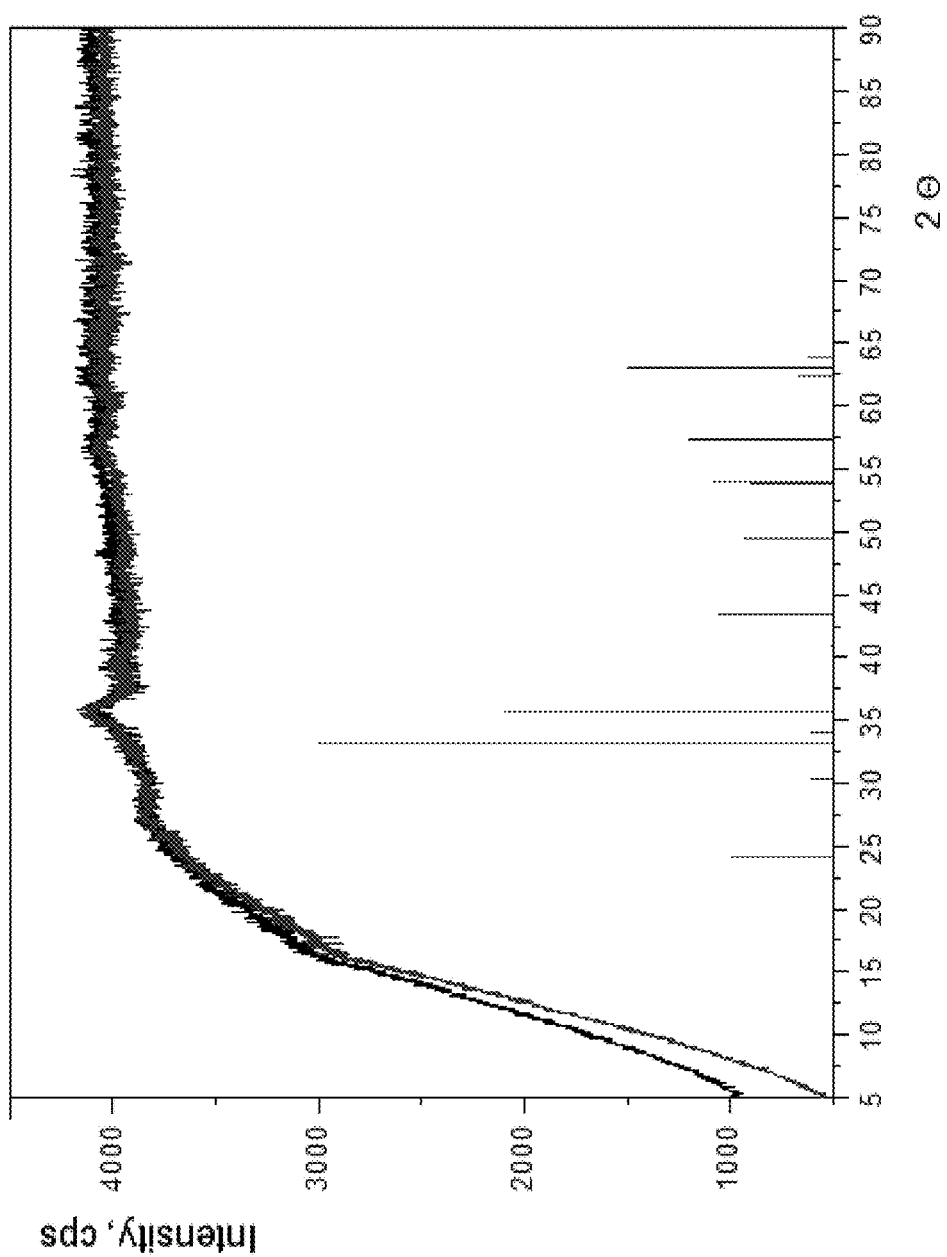
FIG. 12 shows X-ray diffraction (XRD) for iron-polydextrose complex (PDIC) and polysaccharide iron complex (PIC) particulates as described in Example 11.

Results suggest the crystal structure of the iron oxyhydroxide core within PDIC and PIC are composed of akaganéite and hematite crystal structures, or a combination thereof. Results are visually depicted in FIG. 12.

Example 12

Following are details for Fourier transformed infrared (FTIR) spectroscopy performed on a PDIC complex prepared as described in Example 6 and a PIC complex prepared as described in Example 7.

Equipment:
Spectrum 100 FT-IR, PERKINELMER

The PDIC or PIC particulates were placed on top of the ATR crystal and then pressed down using the ATR press with a flat face. The amount of sample used was sufficient to completely cover the ATR crystal.

Following data collection, data requiring library matching, comparative subtractions, or baseline corrections were processed using the KNOWITALL software from BIO-RAD.

Figure 13:
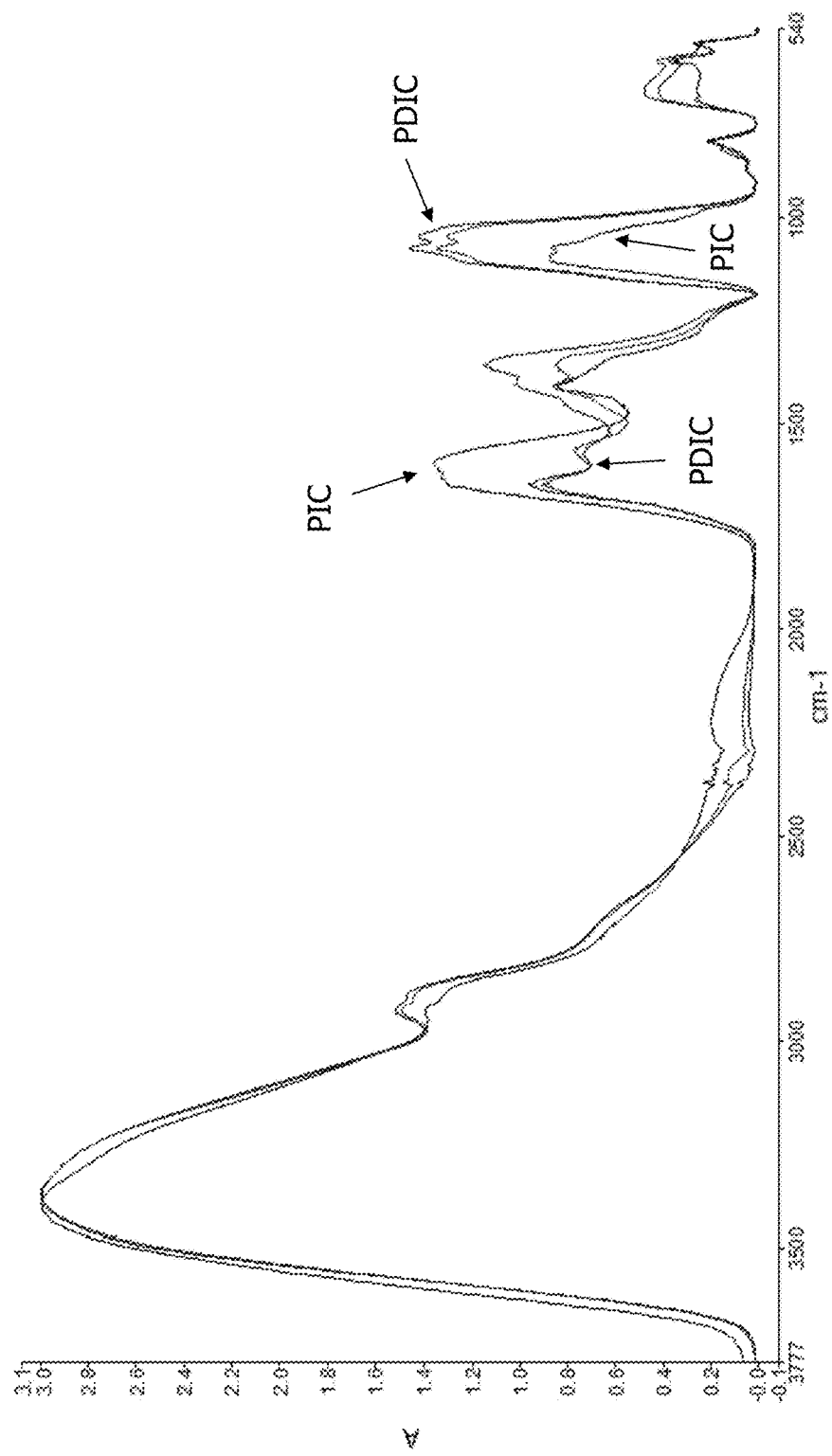
FIGS. 13 and 14 are Fourier transform infrared (FTIR) spectra for iron-polydextrose complex (PDIC) and polysaccharide iron complex (PIC) particulates as described in Example 12.
Figure 14:
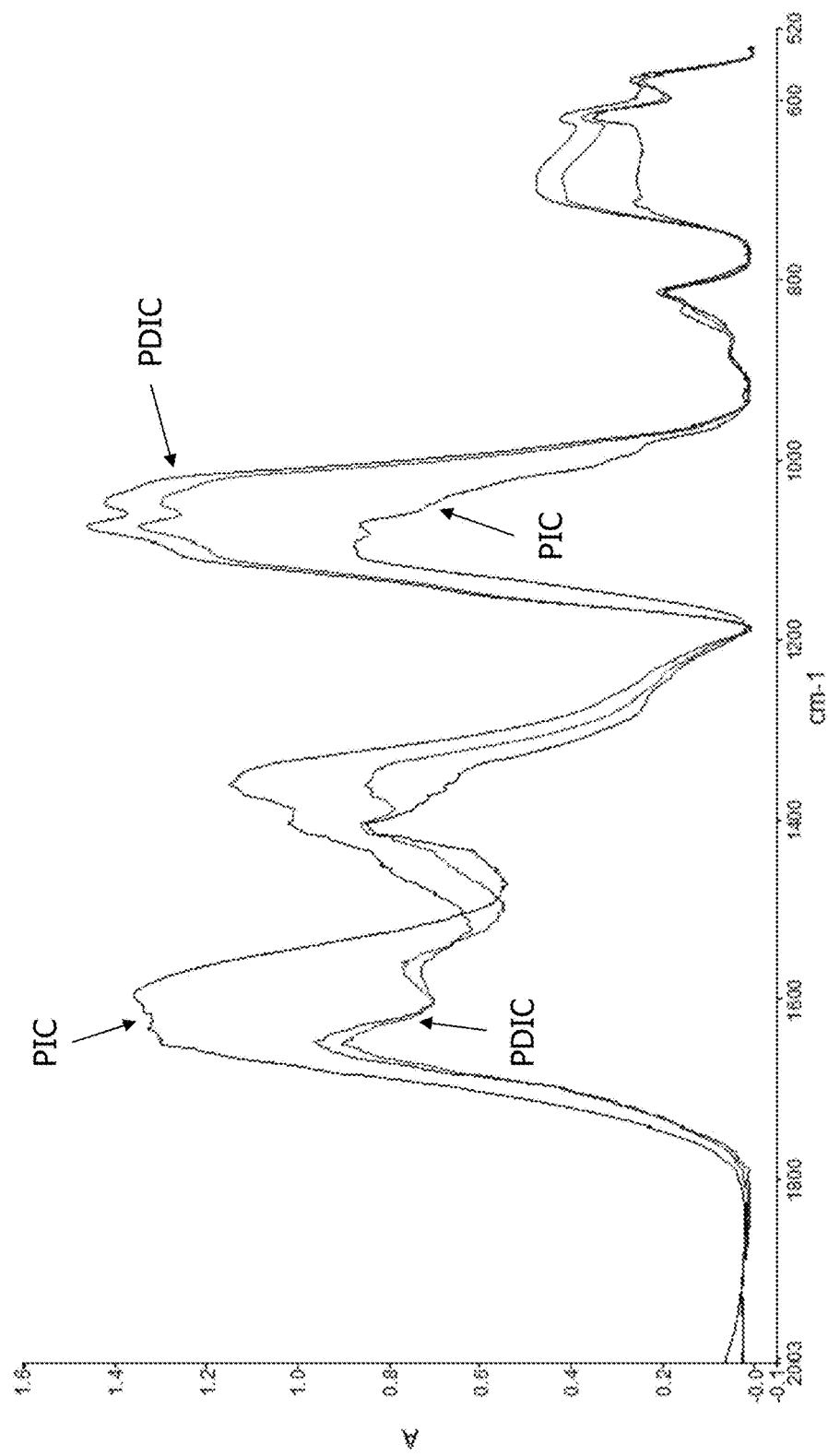

In general, the FTIR spectra for the PDIC and PIC samples in FIG. 13 and FIG. 14 show common features but contain clear distinguishing features, specifically in the ~1600 cm$^{-1}$ and ~1100 cm$^{-1}$ regions. Without being bound by theory, the strong absorbance band near 3300 cm$^{-1}$ (FIG. 13) is believed to correspond to vibrations of the hydroxyl groups. Additionally, and without being bound to any particular theory, the absorbance band between 1200 and 900 cm$^{-1}$ (FIG. 14) is believed to correspond to C—O—C antisymmetric stretching of aliphatic esters and C—O stretch of the alcohols.

The spectrum in FIG. 13 shows an absorbance peak between 1200 and 900 cm$^{-1}$ that is approximately 30% higher for PDIC as compared to PIC, indicating there are more hydroxyl groups present. Additionally, the spectrum in FIG. 13 shows an absorbance peak ~1600 cm$^{-1}$ that is approximately 30% lower for PDIC as compared to PIC, indicating the sugar molecules in PIC are able to stretch and vibrate more because they are less constrained and have more degrees of freedom. Conversely, the sugar molecules in PDIC are not able to stretch and vibrate as much because they are more constrained, as a result of the additional glycosidic linkages, and therefore have less degrees of freedom.

Example 13

Following are details for Raman spectroscopy analysis that was performed on a PDIC complex prepared as described in Example 6 and a PIC complex prepared as described in Example 7.

Equipment:
i-RAMAN, B&WTEK
Raman video microscopy, B&WTEK

The PDIC or PIC particulates were pressed into a small 7 mm diameter pellet using a 2-ton pound press to achieve a flat surface for analysis. Sample integration time and laser power were modulated to achieve the best signal to noise for each sample during analysis. The i-RAMAN system uses a 785 nm laser with a spectral range of 150-3200 cm$^{-1}$. Following data collection, data requiring library matching, comparative subtractions, baseline corrections, or fluorescence correction were processed using the KNOWITALL software from BIO-RAD.

Figure 15:
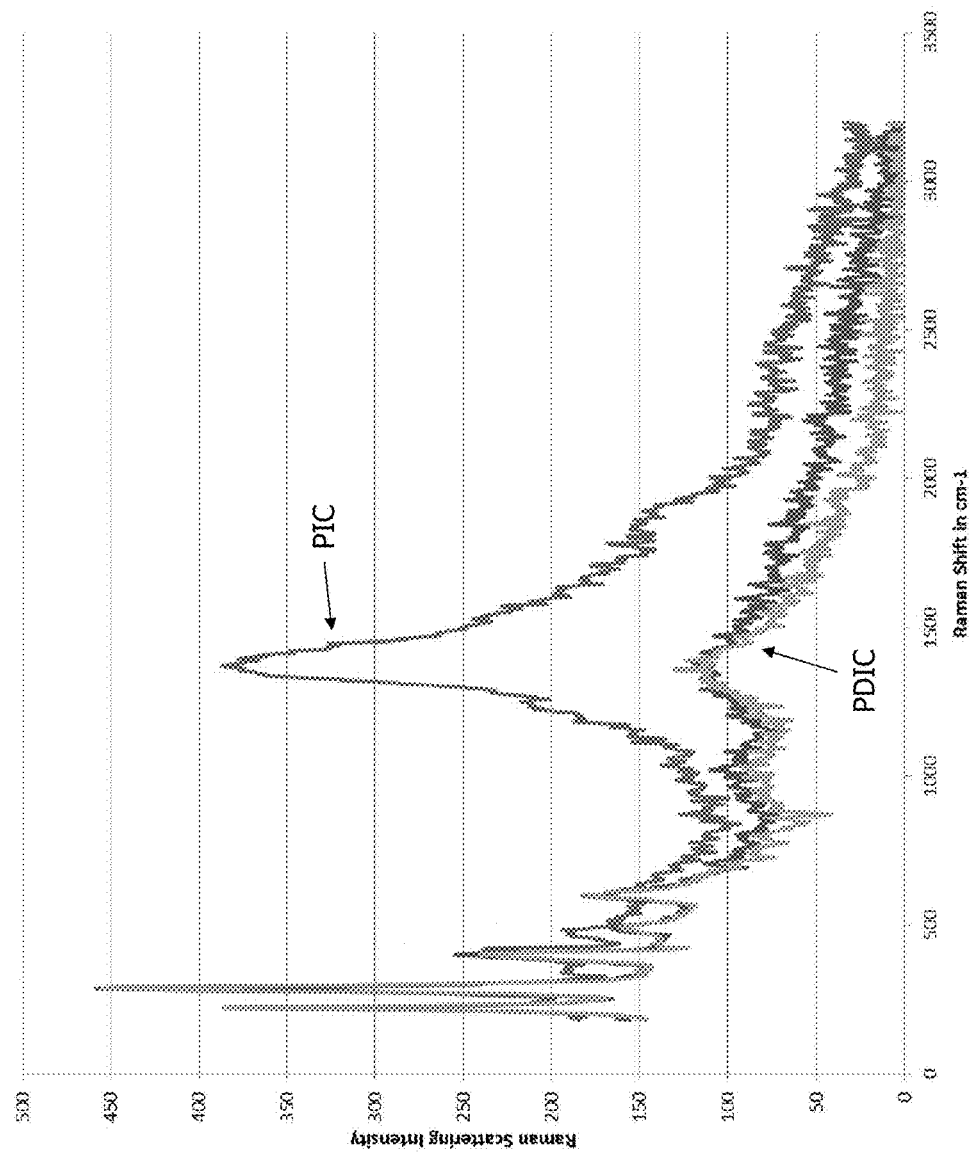
FIG. 15 shows Raman spectroscopy spectra for iron-polydextrose complex (PDIC) and polysaccharide iron complex (PIC) particulates as described in Example 13.

Results are shown in FIG. 15.

In general, the spectra in FIG. 15 show many common features but still contain clear distinguishing features, specifically between 1000 and 2000 cm$^{-1}$. Without being bound by theory, the peak ~1400 cm$^{-1}$ is currently believed to correspond to C—H bending and the peak ~1900 cm$^{-1}$ is currently believed to correspond to C=O stretching. Differences in these regions are expected due to the different sugars that coat the iron oxyhydroxide core, in particular the larger polydextrose sugar molecules are believed to provide greater coating of the iron oxyhydroxide core (i.e., less exposed iron oxyhydroxide within the core at the surface of the PDIC complex).

Example 14

Following are details for molecular size characterization that was performed on a PDIC complex prepared as described in Example 6 and a PIC complex prepared as described in Example 7.

Equipment:
PSS Suprema Analytical 10,000 Å, 8×300 mm, 10 μm, PSS
Guard column, PSS The PDIC or PIC particulates were prepared by dissolving 25 mg of particulate into 100 mL of mobile phase.

The mobile phase was 50 mM phosphate buffer, pH 7.2, and a flow rate of 1.0 mL/minute. The column temperature was set at 25° C. The injection volume was 80 μL. The UV detector was set at 254 nm.

Figure 16:
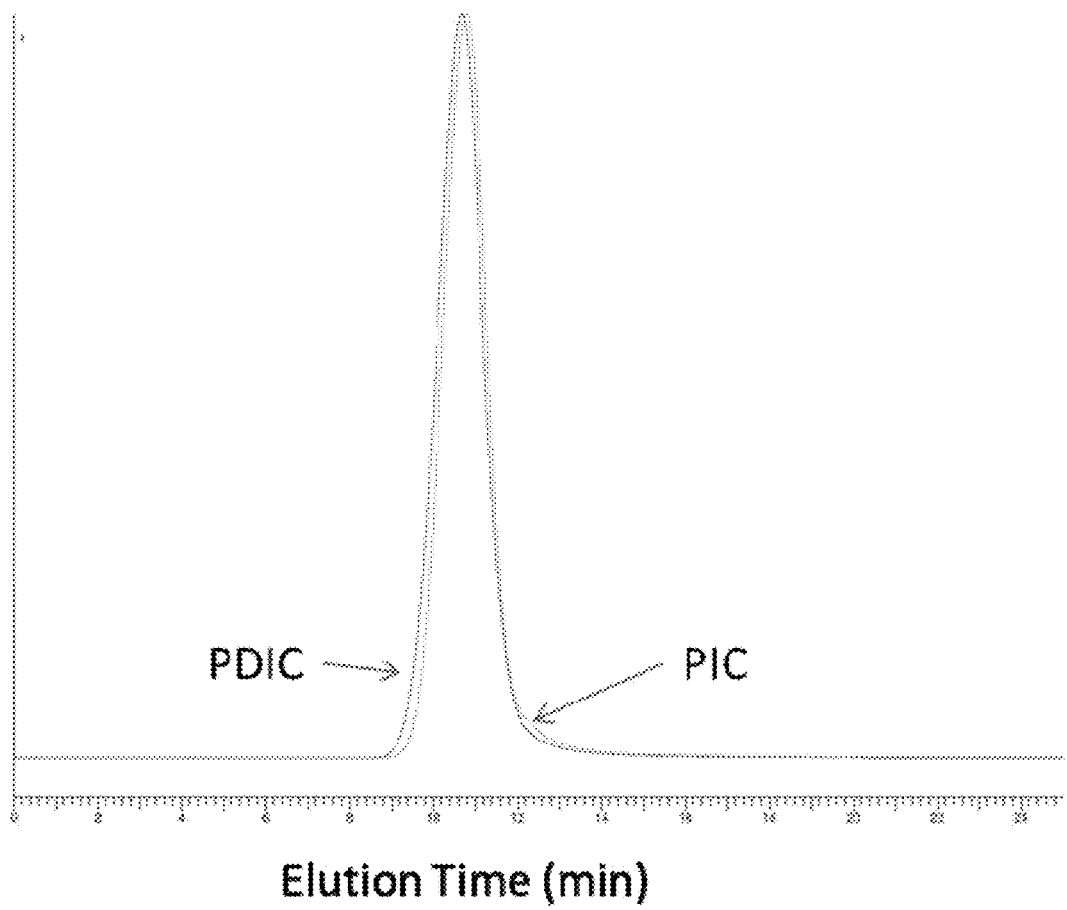
FIG. 16 shows gel permeation chromatography for iron-polydextrose complex (PDIC) and polysaccharide iron complex (PIC) particulates as described in Example 14.

Results are shown in FIG. 16.

In general, the results show very close overlay of the elution curves for both the PDIC and PIC samples. Thus, the PDIC and PIC samples have very close molecular size distributions.

Example 15

Following is a Table summarizing features of samples from the batches prepared in accordance with the method of Example 6.

TABLE 8

|  | Batch 1 | | Batch 2 | | |
| --- | --- | --- | --- | --- | --- |
|  | Drum 1 | Drum 2 | Drum 3 | Drum 4 | Drum 5 |
| NaCl | 2.52% | 2.53% | 3.01% | 3.01% | 2.70% |
| Moisture | 5.52% | 5.69% | 5.78% | 5.58% | 5.76% |
| pH | 11.83 | 11.84 | 11.61 | 11.98 | 12.0 |
| Free Alkali | 7.11 | 7.3 | 8.36 | 8.94 | 8.7 |
| Assay | 41.58% | 41.64% | 40.14% | 39.79% | 39.96% |
| Solubility | 101.89% | 100.15% | 101.90% | 102.60% | 103.36% |

Example 16

Following are details for zeta potential and absolute particle size distribution measurements performed on a PDIC complex prepared as described in Example 6 and a PIC complex prepared as described in Example 7.

Equipment
LITESIZER 500 particle analyzer, Anton-Paar

Samples of both PIC and PDIC were diluted in water (25 mg powder to 100 ml of water) then samples were analyzed. Analysis was conducted following standard protocols.

The parameters determined by the LITESIZER were zeta potential and absolute particle size distribution. Zeta potential is the electric potential in the interfacial double layer (DL) at the location of the slipping plane relative to a point in the bulk fluid away from the interface. In other words, zeta potential is the potential difference between the dispersion medium and the stationary layer of fluid attached to the dispersed particle. It is used as a measure of colloidal stability since a high repulsive force will prevent particle interaction and aggregation. Particle stability is listed in the following table:

TABLE 9

| Zeta potential [mV] | Stability behavior of the colloid |
|---|---|
| from 0 to ±5, | Rapid coagulation or flocculation |
| from ±10 to ±30 | Incipient instability |
| from ±30 to ±40 | Moderate stability |
| from ±40 to ±60 | Good stability |
| more than ±61 | Excellent stability |

Figure 17:
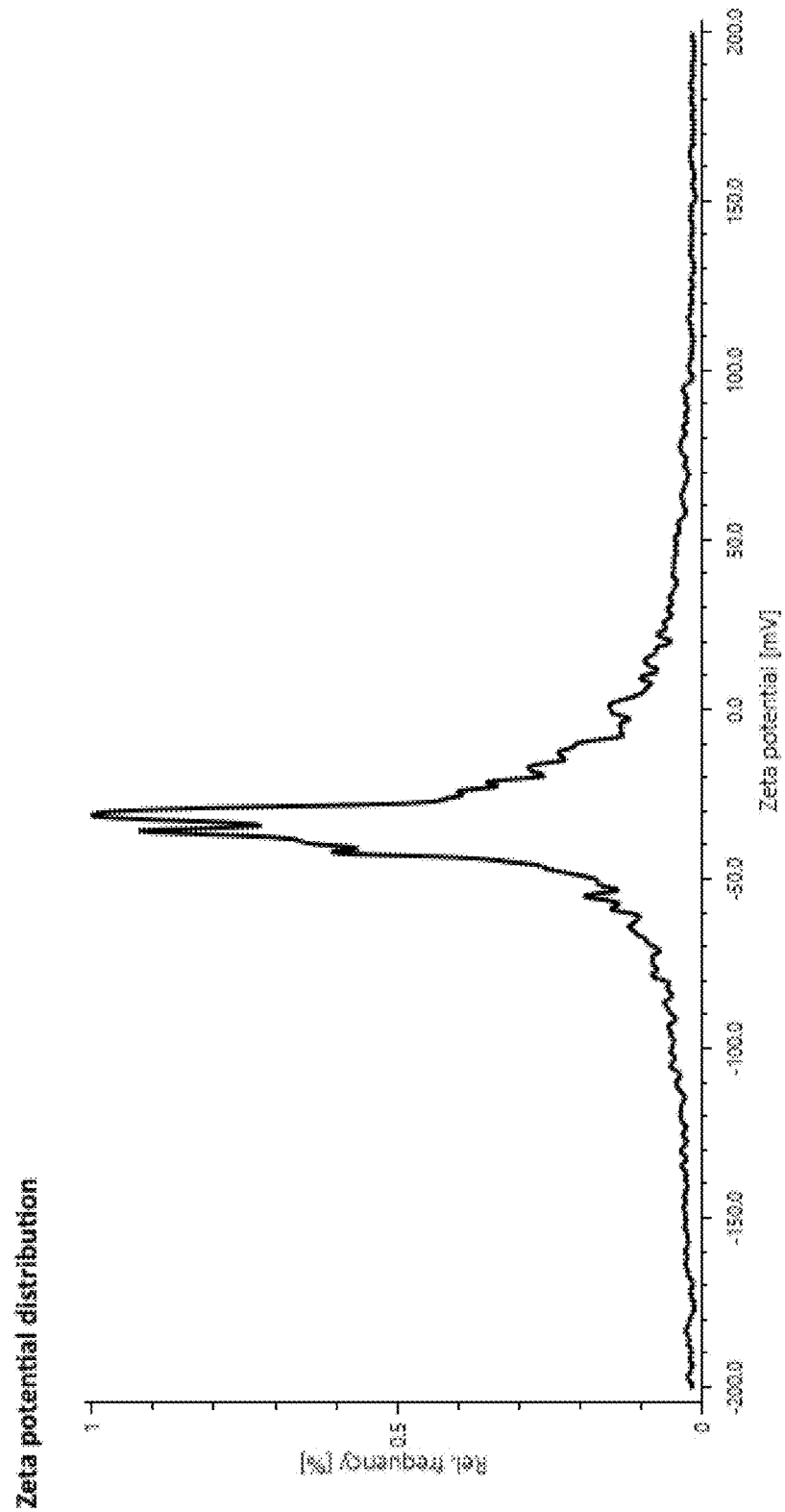
FIGS. 17 and 18 show the zeta potential distribution for polysaccharide iron complex (PIC) and for iron-polydextrose complex (PDIC) particulates as described in Example 16.
Figure 18:
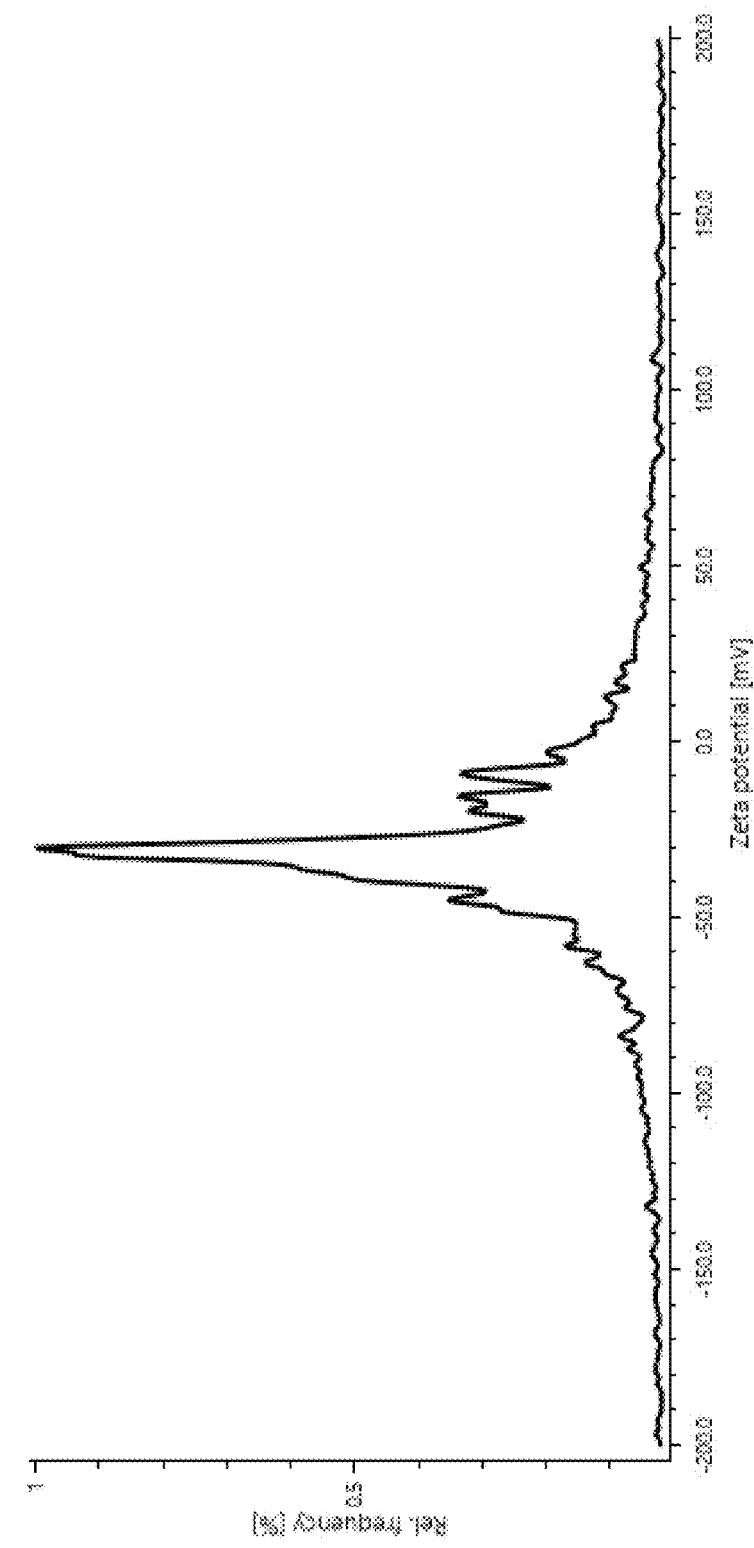

Results from zeta potential analysis are listed in the table below and shown in FIGS. 17 and 18.

TABLE 10

| Sample | Zeta Potential (mV) | |
|---|---|---|
| Type | Mean | Peak |
| PIC | −34.6 | −30.9 |
| PDIC | −29.5 | −30.1 |

The hydrodynamic size measured by dynamic light scattering (DLS) is defined as "the size of a hypothetical hard sphere that diffuses in the same fashion as that of the particle being measured." Due to the irregularities in particle shape, it is not a measure of the actual particle size. Hydrodynamic diameter is an important concept for gel permeation chromatography (GPC) where particle size is measure by movement of the particle through a screening stationary phase.

In DLS the size distribution of molecules or particles is the property of interest. The distribution describes how much material is present at the different size "slices." The mean size and the standard deviation from that mean can be obtained directly from the statistics of the distribution.

Particle size is reported by three different distributions on this instrument, intensity, number, and volume distribution. Intensity distribution is a direct measurement without further manipulation based on particle characteristics. Number distribution and volume distributions take into account particle characteristics like refractive index. Number distribution is unweighted and represents the number of particles in each size bin. Volumedistribution weights each bin by radius cubed, and is an indication of how mass is distributed in the sample.

Results for volume and number particle size distribution analysis are listed in the tables below.

TABLE 11

| Sample | Volume Distribution (nm) | | |
|---|---|---|---|
| Type | D(10) | D(50) | D(90) |
| PIC | 9.783 | 12.726 | 21.077 |
| PDIC | 8.066 | 11.051 | 18.398 |

TABLE 12

| Sample | Number Distribution (nm) | | |
|---|---|---|---|
| Type | D(10) | D(50) | D(90) |
| PIC | 7.375 | 10.916 | 14.650 |
| PDIC | 7.495 | 9.045 | 12.699 |

Embodiments

For further illustration, additional non-limiting embodiments of the present invention are set forth below.

Embodiment A is an iron-polysaccharide complex, the complex comprising iron (III) ions and a polysaccharide, the polysaccharide comprising dextrose units bonded by 1,2-glycosidic linkages, 1,4-glycosidic linkages, and 1,6-glycosidic linkages.

Embodiment B is an iron-polysaccharide complex, the complex comprising iron (III) ions and a polysaccharide, the polysaccharide having a glycemic index of less than about 10.

Embodiment C is an iron-polysaccharide complex, the complex comprising iron (III) ions and a polysaccharide, wherein the polysaccharide has a fiber content of at least about 80% by weight.

Embodiment D is an iron-polysaccharide complex, the complex comprising Fe(III) ions and a polysaccharide, wherein the polysaccharide is non-reactive to anti-dextran antibodies.

Embodiment D1 is the complex of any of embodiments A to D, wherein the polysaccharide is polydextrose.

Embodiment E is an iron-polysaccharide complex, the complex comprising Fe(III) ions and polydextrose as the polysaccharide, the complex comprising Fe(III) ions bonded to the polydextrose.

Embodiment E1 is the complex of any of embodiments A to E, the complex comprising Fe(III)-oxyhydroxide bonded to the polysaccharide.

Embodiment E2 is the complex of any of embodiments A to E1, the complex comprising Fe(III)-oxyhydroxide chelated by the polysaccharide.

Embodiment E3 is the complex of any of embodiments A to E2, wherein the polysaccharide comprises alpha and beta glycosidic linkages.

Embodiment E4 is the complex of any of embodiments A to E3, wherein the polysaccharide comprises straight and branched chains.

Embodiment E5 is the complex of any of embodiments A to E4, wherein the 1,6-glycosidic linkages constitute a majority of the glycosidic linkages of the polysaccharide.

Embodiment E6 is the complex of any of embodiments A to E5, wherein Fe(III)-oxyhydroxide is bonded to the polysaccharide by hydrogen bonds, covalent bonds, or a combination thereof.

Embodiment E7 is the complex of any of embodiments A to E6, wherein Fe(III) ions are chelated by the polysaccharide.

Embodiment E8 is the complex of any of embodiments A to E7, wherein Fe(III)-oxyhydroxide is chelated by the polysaccharide.

Embodiment E9 is the complex of any of embodiments A to E8, the complex further comprising sorbitol.

Embodiment E10 is the complex of embodiment E9, wherein the sorbitol is bonded to the polysaccharide.

Embodiment E11 is the complex of any of embodiments A to E10, wherein the polysaccharide has a glycemic index of less than about 10, less than about 8, or less than about 6.

Embodiment E12 is the complex of any of embodiments A to E11, wherein the polysaccharide is polydextrose, the complex comprising Fe(III)-oxyhydroxide bonded to polydextrose.

Embodiment E13 is the complex of any of embodiments A to E12, wherein the polydextrose has a molecular weight of from about 150 to about 20,000 Da.

Embodiment E14 is the complex of any of embodiments A to E13, wherein at least about 90% (by weight) of the polydextrose molecules have a molecular weight of from about 500 to about 5,000 Da.

Embodiment E15 is the complex of any of embodiments A to E14, wherein the average degree of polymerization of the polydextrose is from about 10 to about 15 or about 12, and the average molecular weight of the polydextrose is from about 1,800 to about 2,200 Da, or about 2,000 Da.

Embodiment E16 is the complex of any of embodiments A to E15, wherein the polydextrose has a fiber content of at least about 80% or at least about 90%.

Embodiment E17 is the complex of any of embodiments A to E16, wherein the polydextrose is non-reactive to anti-dextran antibodies.

Embodiment E18 is the complex of any of embodiments A to E17, wherein the polydextrose is pharmaceutical grade or food grade.

Embodiment E19 is the complex of embodiment E18, wherein the polydextrose is food grade.

Embodiment E20 is the complex of any of embodiments A to E19, wherein the weight ratio of iron (III) ions to polydextrose is from about 0.1:1 to about 10:1, from about 0.3:1 to about 3:1, or from about 0.5:1 to about 2:1.

Embodiment E21 is the complex of any of embodiments A to E20, wherein the Fe(III)-oxyhydroxide polydextrose complex comprises an Fe(III)-oxyhydroxide core with a diameter in its largest dimension of from about 2 nm to about 20 nm.

Embodiment E22 is the complex of any of embodiments A to E21, wherein the Fe(III)-oxyhydroxide polydextrose complex comprises an Fe(III)-oxyhydroxide core with a diameter in its largest dimension of from about 10 nm to about 15 nm.

Embodiment E23 is the complex of any of embodiments A to E22, wherein the Fe(III)-oxyhydroxide iron core is spheroid, ellipsoid, spherical or rod-like in shape.

Embodiment E24 is the complex of any of embodiments A to E23, wherein the Fe(III)-oxyhydroxide iron core is spherical in shape.

Embodiment E25 is the complex of any of embodiments A to E24, wherein the Fe(III)-oxyhydroxide polydextrose complex has a diameter in its largest dimension of from about 1 nm to about 30 nm.

Embodiment E26 is the complex of any of embodiments A to E25, wherein the complex has a density of about 4 g/cm$^3$ or about 5 g/cm$^3$.

Embodiment E27 is the complex of any of embodiments A to E26, wherein Fe(III) is coordinated by two oxygen atoms.

Embodiment E28 is the complex of any of embodiments A to E27, wherein the Fe(III) oxygen bond distance is about 1.9 Å.

Embodiment E29 is the complex of any of embodiments A to E28, the complex having an Fe(III) content of at least about 25 weight %, at least about 30 weight %, at least about 35 weight %, or at least about 40 weight %.

Embodiment E30 is the complex of any of embodiments A to E29, the complex having an Fe(III) content of from about 20 to about 50 weight %, from about 30 to about 50 weight %, from about 40 to about 50 weight %, or from about 45 to about 50 weight %.

Embodiment E31 is the complex of any of embodiments A to E30, wherein the Fe(III)-oxyhydroxide is present in an amount of from about 50 to about 95 weight % or from about 50 to about 70 weight %.

Embodiment E32 is the complex of any of embodiments A to E31, the complex having a polysaccharide content of at least about 5 weight %, at least about 10 weight %, at least about 20 weight %, or at least about 30 weight %.

Embodiment E33 is the complex of any of embodiments A to E32, the complex having a polysaccharide content of from about 5 to about 40 weight %, from about 10 to about 40 weight %, or from about 20 to about 40 weight %.

Embodiment E34 is the complex of any of embodiments A to E33, wherein the Fe(III)-oxyhydroxide polydextrose complex has a molecular weight from about 10 KDa to about 200,000 KDa.

Embodiment E35 is the complex of any of embodiments A to E34, wherein the Fe(III)-oxyhydroxide polydextrose complex has a molecular weight from about 10 KDa to about 200,000 KDa, from about 10 to about 100,000 kDa, from about 100 to about 50,000 KDa, from about 500 about 25,000 KDa, from about 500 to about 20,000 KDa, or about 10,000 KDa.

Embodiment F is an iron-polysaccharide complex, the complex comprising iron (III) ions and polydextrose, the polydextrose comprising dextrose units bonded by 1,2-glycosidic linkages, 1,4-glycosidic linkages, and 1,6-glycosidic linkages, the complex comprising Fe(III) ions bonded to the polydextrose, wherein the complex comprises at least about 0.25 g Fe(III) ions per g of complex.

Embodiment G is a particulate composition comprising iron (III) ions and a polysaccharide, the iron (III) ions and polysaccharide in the form of a complex with the iron (III) ions bonded to the polysaccharide, and wherein the polysaccharide comprises polydextrose.

Embodiment G1 is the particulate composition of embodiment G, wherein the moisture content is no more than about 10 weight %, or from about 4 weight % to about 8 weight %.

Embodiment G2 is the particulate composition of embodiment G or G1 having a particle size distribution such that at least about 50% (weight basis) of the particles have a particle size in a range of from about 0.1 µm to about 50 µm.

Embodiment G3 is the particulate composition of any of embodiments G to G2 having a particle size distribution such that at least about 50% (weight basis) of the particles have a particle size in a range of from about 1 µm to about 50 µm.

Embodiment G4 is the particulate composition of any of embodiments G to G3 having a particle size distribution such that at least about 50% (weight basis), at least about 60% (weight basis), at least about 70% (weight basis), at least about 80% (weight basis), or at least about 90% (weight basis) of the particles have a particle size in a range of from about 1 µm to about 30 µm.

Embodiment G5 is the particulate composition of any of embodiments G to G4 having a particle size distribution such that at least about 50% (weight basis) of the particles have a particle size in a range of from about 5 µm to about 30 µm, from about 5 µm to about 25 µm, from about 5 µm to about 20 µm, or from about 10 µm to about 20 µm.

Embodiment G6 is the particulate composition of any of embodiments G to G5 having a particle size distribution such that at least about 60% (weight basis), at least about 70% (weight basis), at least about 80% (weight basis), or at least about 90% (weight basis) of the particles have a particle size in a range of from about 10 µm to about 20 µm.

Embodiment G7 is the particulate composition of any of embodiments G to G6, wherein Fe (III) constitutes from about 30 weight % to about 50 weight % of the particulate composition.

Embodiment G8 is the particulate composition of any of embodiments G to G7, wherein Fe(III) constitutes from about 35 weight % to about 50 weight % of the particulate composition, from about 40 weight % to about 50 weight % of the particulate composition, or from about 44 weight % to about 48 weight % of the particulate composition.

Embodiment G9 is the particulate composition of any of embodiments G to G8, the particulate composition comprising an aggregate of Fe(III)-oxyhydroxide polydextrose complexes.

Embodiment G10 is the particulate composition of any of embodiments G to G9, wherein a plurality of the Fe(III)-oxyhydroxide polydextrose complexes include an Fe(III)-oxyhydroxide core having a diameter in its largest dimension of from about 2 nm to about 15 nm.

Embodiment G11 is the particulate composition of any of embodiments G to G10, wherein a plurality of the Fe(III)-oxyhydroxide polydextrose complexes include an Fe(III)-oxyhydroxide core having a diameter in its largest dimension of from about 5 nm to about 10 nm.

Embodiment G12 is the particulate composition of any of embodiments G to G11, wherein a plurality of the Fe(III)-oxyhydroxide polydextrose complexes have a diameter in their largest dimension of from about 10 nm to about 15 nm.

Embodiment G13 is the particulate composition of any of embodiments G to G12 having a water solubility at neutral pH of at least about 1 mg/ml, at least about 5 mg/ml, at least about 10 mg/ml, or at least about 15 mg/ml.

Embodiment G14 is the particulate composition of any of embodiments G to G13, the composition having a sodium chloride content of no more than about 3.5 weight % or more than about 2 weight %.

Embodiment G15 is the particulate composition of any of embodiments G to G14, the composition having a free Fe(III) content of no more than about 0.5 weight %.

Embodiment G16 is the particulate composition of any of embodiments G to G15 having a total microbial count of no more than about 1000 cfu/g, no more than about 500 cfu/g, no more than about 100 cfu/g, no more than about 50 cfu/g, no more than about 25 cfu/g, or no more than about 1 cfu/g.

Embodiment G17 is the particulate composition of any of embodiments G to G16 having a yeast and mold count of no more than about 100 cfu/g, no more than about 50 cfu/g, no more than about 25 cfu/g, no more than about 10 cfu/g, no more than about 5 cfu/g, or no more than about 1 cfu/g.

Embodiment G18 is the particulate composition of any of embodiments G to G17 having a measured pH value of about 1 to about 14, about 7 to about 14, or about 9 to about 11.

Embodiment H is a method for the preparation of an iron-polysaccharide complex, the method comprising:
  introducing into an aqueous medium a source of iron (III) ions and a polysaccharide comprising polydextrose, thereby forming an aqueous reaction medium comprising Fe(III) ions and polydextrose;
  introducing into the aqueous reaction medium a source of hydroxide ions, thereby forming Fe(III)-oxyhydroxide (ferric oxyhydroxide); and
  adjusting the pH of the aqueous reaction medium, thereby forming an iron-polysaccharide complex comprising Fe(III)-oxyhydroxide and the polysaccharide.

Embodiment H1 is the method of embodiment H, the method further comprising introducing sorbitol into the aqueous reaction medium.

Embodiment H2 is the method of embodiment H or H1, wherein the polydextrose comprises free glucose, sorbitol, citric acid, and/or levoglucosan.

Embodiment H3 is the method of any of embodiments H to H2, wherein the polydextrose comprises dextrose, sorbitol, and citric acid or phosphoric acid.

Embodiment H4 is the method of any of embodiments H to H3, wherein the polydextrose comprises about 90 parts dextrose, about 10 parts sorbitol, and about 1 part citric acid or about 0.1 part phosphoric acid.

Embodiment H5 is the method of any of embodiments H to H4, wherein the polydextrose contains no more than about 5 weight % free glucose.

Embodiment H6 is the method of any of embodiments H to H5, wherein the polydextrose contains no more than about 3 weight % free sorbitol.

Embodiment H7 is the method of any of embodiments H to H6, wherein the polydextrose contains no more than about 1 weight % free citric acid.

Embodiment H8 is the method of any of embodiments H to H7, wherein the polydextrose contains no more than about 5 weight % free levoglucosan.

Embodiment H9 is the method of any of embodiments H to H8, wherein the Fe(III)-oxyhydroxide and the polysaccharide are bonded together by hydrogen bonds and/or covalent bonds in the iron-polysaccharide complex.

Embodiment H10 is the method of any of embodiments H to H9, wherein the source of hydroxide ions introduced into the aqueous reaction medium for formation of Fe(III)-oxyhydroxide (ferric oxyhydroxide) is selected from the group consisting of sodium hydroxide, potassium hydroxide, ammonium hydroxide, and combinations thereof.

Embodiment H11 is the method of any of embodiments H to H10, wherein the source of hydroxide ions introduced into the aqueous reaction medium for formation of Fe(III)-oxyhydroxide (ferric oxyhydroxide) is introduced at a rate of at least about 10 Kg/min, at least about 25 Kg/min, from about 10 Kg/min to about 50 Kg/min, or from about 20 Kg/min to about 50 Kg/min.

Embodiment H12 is the method of any of embodiments H to H11, wherein the source of hydroxide ions introduced into the aqueous reaction medium for formation of Fe(III)-oxyhydroxide (ferric oxyhydroxide) is introduced at a rate of at least about 100 g/min or from about 100 to about 300 g/min.

Embodiment H13 is the method of any of embodiments H to H12, wherein the pH of the aqueous reaction medium during formation of Fe(III)-oxyhydroxide (ferric oxyhydroxide) is less than about 5, less than about 4, or less than about 3.

Embodiment H14 is the method of any of embodiments H to H13, wherein the pH of the aqueous reaction medium during formation of Fe(III)-oxyhydroxide (ferric oxyhydroxide) is from about 1 to about 6, from about 3 to about 5, or from about 3 to about 4.

Embodiment H15 is the method of any of embodiments H to H14, wherein the temperature of the aqueous reaction medium during formation of Fe(III)-oxyhydroxide (ferric oxyhydroxide) is from about 15° C. to about 75° C., from about 20° C. to about 70° C., or from about 20° C. to about 60° C.

Embodiment H16 is the method of any of embodiments H to H15, wherein the aqueous reaction medium is agitated during formation of Fe(III)-oxyhydroxide (ferric oxyhydroxide) by an impeller operated at a rate of from about 100 to about 2000 revolutions per minute (RPM).

Embodiment H17 is the method of any of embodiments H to H16, wherein the pH of the aqueous reaction medium is adjusted for formation of the iron-polysaccharide complex by addition of a source of hydroxide ions.

Embodiment H18 is the method of any of embodiments H to H17, wherein the pH is adjusted for complex addition by the same source of hydroxide ions introduced for formation of Fe(III)-oxyhydroxide (ferric oxyhydroxide).

Embodiment H19 is the method of any of embodiments H to H18, wherein the Fe(III)-oxyhydroxide (ferric oxyhydroxide) is formed and the pH is adjusted for formation of the iron-polysaccharide complex by separate additions of sources of hydroxide ions.

Embodiment H20 is the method of any of embodiments H to H19, wherein the Fe(III)-oxyhydroxide (ferric oxyhydroxide) is formed and the pH is adjusted for formation of the iron-polysaccharide complex by a single addition of hydroxide ions.

Embodiment H21 is the method of any of embodiments H to H20, wherein the source of hydroxide ions is selected from the group consisting of sodium hydroxide, potassium hydroxide, ammonium hydroxide, and combinations thereof.

Embodiment H22 is the method of any of embodiments H to H21, wherein the source of hydroxide ions is sodium hydroxide.

Embodiment H23 is the method of any of embodiments H to H22, wherein the source of hydroxide ions is a 50 weight % solution of sodium hydroxide.

Embodiment H24 is the method of any of embodiments H to H23, wherein the source of hydroxide ions introduced into the aqueous reaction medium for adjustment of the pH of the aqueous reaction medium is introduced at a rate of at least about 10 Kg/min, at least about 25 Kg/min, from about 10 Kg/min to about 50 Kg/min, or from about 20 Kg/min to about 50 Kg/min.

Embodiment H25 is the method of any of embodiments H to H24, wherein the source of hydroxide ions introduced into the aqueous reaction medium for formation of Fe(III)-oxyhydroxide (ferric oxyhydroxide) is introduced at a rate of at least about 100 g/min or from about 100 to about 300 g/min.

Embodiment H26 is the method of any of embodiments H to H25, wherein the pH of the aqueous reaction medium during formation of the iron-polysaccharide complex is at least about 4, at least about 5, or at least about 6.

Embodiment H27 is the method of any of embodiments H to H26, wherein the pH of the aqueous reaction medium during formation of the iron-polysaccharide complex is from about 4 to about 13, from about 5 to about 12, or from about 6 to about 12.

Embodiment H28 is the method of any of embodiments H to H27, wherein the temperature of the aqueous reaction medium during formation of the iron-polysaccharide complex is from about 50° C. to about 120° C., from about 60° C. to about 110° C., or from about 70° C. to about 100° C.

Embodiment H29 is the method of any of embodiments H to H28, wherein the source of Fe(III) ions is selected from the group consisting of ferric chloride, ferric sulfate, ferric citrate, ferric nitrate, ferric ammonium sulfate, ferric nitrate, and combinations thereof.

Embodiment H30 is the method of any of embodiments H to H29, wherein the weight ratio of Fe(III) ions to polydextrose introduced into the aqueous reaction medium is at least about 0.1:1, at least about 0.2:1, or at least about 0.3:1.

Embodiment H31 is the method of any of embodiments H to H30, wherein the weight ratio of Fe(III) ions to polydextrose introduced into the aqueous reaction medium is from about 0.1:1 to about 5:1, from about 0.3:1 to about 3:1, or from about 0.5:1 to about 2:1.

Embodiment H32 is the method of embodiment H31, wherein the aqueous reaction medium comprising the iron-polydextrose complex is allowed to cool to a temperature of less than about 70° C., less than about 60° C., or less than about 50° C., thereby forming an iron-polydextrose product slurry.

Embodiment H33 is the method of any of embodiments H to H32, wherein the iron-polydextrose product slurry has a moisture content of at least about 30 weight %, at least about 40 weight %, from about 30 to about 95 weight %, or from about 40 to about 95 weight %.

Embodiment H34 is the method of any of embodiments H to H33, wherein an iron-polydextrose product mixture is recovered from the iron-polydextrose product slurry by a filtration operation, chromatographic separation, or precipitation.

Embodiment H35 is the method of any of embodiments H to H34, wherein the iron-polydextrose slurry is filtered to provide an iron-polydextrose product mixture having a moisture content of less than about 80 weight %, less than about 70 weight %, or less than about 60 weight %.

Embodiment H36 is the method of any of embodiments H to H35, wherein filtration of the iron-polydextrose slurry is by ultrafiltration using an ultrafiltration membrane having a molecular weight cut-off of from about 10,000 Da to about 100,000 Da.

Embodiment H37 is the method of any of embodiments H to H36, wherein the iron-polydextrose product mixture is spray dried to form a particulate iron-polydextrose product.

Embodiment H38 is the method of any of embodiments H to H37 wherein the temperature of the reaction medium does not increase more than about 40° C. from addition of the first source of hydroxide ions to completion of mixing following introduction of the second source of hydroxide ions.

Embodiment H39 is the method of any of embodiments of H to H38 wherein the temperature of the reaction medium during a second addition of hydroxide ions and mixing is no greater than about 90° C.

Embodiment I is a method for treatment of iron deficient anemia, the method comprising administering to a subject in need thereof a composition or complex as defined in any of the preceding claims.

Embodiment J is a method for treatment of iron deficient anemia and constipation, the method comprising administering to a subject in need thereof a composition or complex as defined in any of the preceding claims.

Embodiment K is a method for fiber supplementation, the method comprising administering to a subject in need thereof a composition or complex as defined in any of the preceding claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above description without departing from the scope of the invention, it is intended that all matter contained in the above description and shown in the accompanying Figures shall be interpreted as illustrative and not in a limiting sense.

What is claimed is:

1. A particulate composition comprising an iron-polydextrose complex, wherein:
   the iron (Fe) content of the composition is at least about 30 wt %; and
   the ratio of C:Fe, as determined by elemental analysis, is at least 0.2:1, wherein the iron-polydextrose complex is prepared by a process comprising:
   introducing into an aqueous medium a source of iron (III) ions and polydextrose, thereby forming an aqueous reaction medium comprising Fe(III) ions and polydextrose, wherein the weight ratio of the source of iron (III) ions to polydextrose introduced into the aqueous medium is from about 0.5:1 to about 2:1;
   introducing into the aqueous reaction medium a first source of hydroxide ions and mixing the contents of the reaction medium, thereby forming Fe(III)oxyhydroxide; and
   introducing into the aqueous reaction medium a second source of hydroxide ions and mixing the contents of the reaction medium, thereby forming the iron-polydextrose complex, and wherein:
   the temperature of the reaction medium does not increase more than about 40° C. from addition of the first source of hydroxide ions to completion of the mixing following introduction of the second source of hydroxide ions.

2. The composition of claim 1, wherein the complex has a carbon content, as determined by elemental analysis, of at least about 3%.

3. The composition of claim 1, wherein the complex has a carbon content, as determined by elemental analysis, of from about 3% to about 20%.

4. The composition of claim 1, wherein the Fe content of the composition is at least about 35 wt %.

5. The composition of claim 1, wherein the Fe content of the composition is from about 30 wt % to about 50 wt %.

6. A particulate composition comprising an iron-polydextrose complex, wherein:
   the iron (Fe) content of the composition is at least about 30 wt %; and
   the ratio of C:Fe, as determined by elemental analysis, is at least 0.2:1, wherein the iron-polydextrose complex is prepared by a process comprising:
   introducing into an aqueous medium a source of iron (III) ions and polydextrose, thereby forming an aqueous reaction medium comprising Fe(III) ions and polydextrose, wherein the weight ratio of the source of iron (III) ions to polydextrose introduced into the aqueous medium is from about 0.5:1 to about 2:1;
   introducing into the aqueous reaction medium a first source of hydroxide ions and mixing the contents of the reaction medium; and
   introducing into the aqueous reaction medium a second source of hydroxide ions and mixing the contents of the reaction medium, thereby forming the iron-polydextrose complex, and wherein:
   the temperature of the reaction medium during the second addition of hydroxide ions and mixing is no greater than about 90° C.

7. The composition of claim 1, wherein the complex has a carbon content, as determined by elemental analysis, of at least about 7%.

8. The composition of claim 1, wherein the complex has a carbon content, as determined by elemental analysis, of at least about 10%.

9. The composition of claim 1, wherein the ratio of C:Fe, as determined by elemental analysis, is at least about 0.25:1.

10. The composition of claim 1, wherein the ratio of C:Fe, as determined by elemental analysis, is at least about 0.3:1.

11. The composition of claim 1, wherein the Fe content of the composition is at least about 40 wt %.

12. The composition of claim 1, wherein the Fe content of the composition is at least about 45 wt %.

13. The composition of claim 1 wherein the Fe content of the composition is from about 42 wt % to about 48 wt %.

14. The composition of claim 1, wherein the iron-polydextrose complex comprises an iron oxyhydroxide-containing core bound to one or more polydextrose molecules.

15. The composition of claim 1, wherein polydextrose molecules of the iron-polydextrose complex comprise dextrose units bonded by 1,2-glycosidic linkages, 1,4-glycosidic linkages, and 1,6-glycosidic linkages.

16. The composition of claim 1, wherein the iron-polydextrose complex comprises Fe(III)-oxyhydroxide bonded to the polydextrose.

17. The composition of claim 16, wherein the Fe(III)-oxyhydroxide is bonded at its hydroxyl, oxy, and metal sites to hydroxyl sites of the polydextrose.

18. The composition of claim 1, wherein the iron-polydextrose complex comprises Fe(III) ions bonded to the polydextrose.

19. The composition of claim 15, wherein 1,6-glycosidic linkages constitute a majority of the linkages between the dextrose units of the polydextrose.

20. The composition of claim 6, wherein the complex has a carbon content, as determined by elemental analysis, of at least about 7%.

21. The composition of claim 6, wherein the complex has a carbon content, as determined by elemental analysis, of at least about 10%.

22. The composition of claim 6, wherein the complex has a carbon content, as determined by elemental analysis, of from about 3% to about 20%.

23. The composition of claim 6, wherein the Fe content of the composition is at least about 40 wt %.

24. The composition of claim 6, wherein the Fe content of the composition is from about 30 wt % to about 50 wt %.

25. The composition of claim 6, wherein the Fe content of the composition is from about 42 wt % to about 48 wt %.

26. The composition of claim 6, wherein the ratio of C:Fe, as determined by elemental analysis, is at least about 0.25:1.

27. The composition of claim 6, wherein the ratio of C:Fe, as determined by elemental analysis, is at least about 0.3:1.

28. The composition of claim 6, wherein polydextrose molecules of the iron-polydextrose complex comprise dextrose units bonded by 1,2-glycosidic linkages, 1,4-glycosidic linkages, and 1,6-glycosidic linkages.

29. The composition of claim 28, wherein 1,6-glycosidic linkages constitute a majority of the linkages between the dextrose units of the polydextrose.

* * * * *